United States Patent
Li et al.

(10) Patent No.: US 6,723,445 B2
(45) Date of Patent: Apr. 20, 2004

(54) ORGANIC LIGHT-EMITTING DEVICES

(75) Inventors: Xiao-Chang Charles Li, Union City, CA (US); Bing R. Hsieh, Webster, NY (US)

(73) Assignee: Canon Kabushiki Kaisha, Tokyo (JP)

( * ) Notice: Subject to any disclaimer, the term of this patent is extended or adjusted under 35 U.S.C. 154(b) by 29 days.

(21) Appl. No.: 10/029,671

(22) Filed: Dec. 31, 2001

(65) Prior Publication Data

US 2003/0138662 A1 Jul. 24, 2003

(51) Int. Cl.[7] .................. H05B 33/12; C07D 241/36
(52) U.S. Cl. .................. 428/490; 428/917; 313/504; 313/506; 544/338; 544/343; 544/339
(58) Field of Search ................ 428/690, 917; 313/502, 506, 504; 544/353, 338, 343, 339

(56) References Cited

U.S. PATENT DOCUMENTS

| | | | |
|---|---|---|---|
| 2,988,549 A | 6/1961 | Hawthorne et al. | 260/250 |
| 3,534,041 A | 10/1970 | Van Der | 260/268 |
| 4,184,977 A | 1/1980 | Eckstein et al. | 252/301.22 |
| 5,306,587 A | 4/1994 | Terrell et al. | 430/58 |
| 5,350,644 A | 9/1994 | Graetzel et al. | 429/111 |
| 5,755,999 A | 5/1998 | Shi et al. | 252/301.16 |
| 5,792,567 A | 8/1998 | Kido et al. | 428/690 |
| 5,861,219 A | 1/1999 | Thompson et al. | 428/690 |
| 5,879,821 A | 3/1999 | Hsieh | 428/690 |
| 5,904,994 A | 5/1999 | Dodabalapur et al. | 428/690 |
| 5,925,472 A | 7/1999 | Hu et al. | 428/690 |
| 5,955,836 A | 9/1999 | Boerner et al. | 313/506 |
| 6,023,371 A | 2/2000 | Onitsuka et al. | 359/620 |
| 6,150,042 A | 11/2000 | Tamano et al. | 428/690 |
| 6,165,383 A | 12/2000 | Chou | 252/301.16 |
| 6,180,267 B1 * | 1/2001 | Toguchi et al. | 428/690 |
| 6,245,449 B1 | 6/2001 | Tamano et al. | 428/690 |
| 6,255,449 B1 | 7/2001 | Woo et al. | 528/401 |
| 6,259,202 B1 | 7/2001 | Sturm et al. | 313/504 |

(List continued on next page.)

FOREIGN PATENT DOCUMENTS

| | | |
|---|---|---|
| DE | 196 46 119 A1 * | 5/1998 |
| JP | 9013025 | 1/1997 |
| JP | 09-188874 | 7/1997 |

OTHER PUBLICATIONS

Cohen, Yoram et al., "New Polyheterocyclic 4n pi–Electron Dianions: Paratropicity, Charge Delocalization, and Reactions" (1986), Journal of the American Chemical Society, vol. 108, pp. 7039–7044.*

"Phenylquinoxaline Polymers and Low Molar Mass Glasses as Electron–Transport Materials in Organic Light–Emitting Diodes," Jandke, et al., Macromolecules 1998, 31, 6434–6443.

"Design and Application of Electron–Transporting Organic Materials" Strukelj, et al., Science, vol. 267, Mar. 31, 1995.

"High Electron Mobility In Bathophenanthroline" Naka, et al., American Institute of Physics, pp. 197–199, 2000.

Primary Examiner—Dawn Garrett
(74) Attorney, Agent, or Firm—Fitzpatrick, Cella, Harper & Scinto

(57) ABSTRACT

Electron transporting materials and organic light emitting devices utilizing the electron transporting materials, wherein the electron transporting materials are dibenzoquinoxaline compounds, and the devices utilize at least one layer incorporating a dibenzoquinoxaline compound. Dibenzoquinoxaline compounds include dipyridyl substituted dibenzoquinoxaline compounds, diphenyl substituted dibenzoquinoxaline compounds, naphthalene substituted dibenzoquinoxaline compounds, anthrene-dibeanzoquinoxaline compounds, bis(methoxy)phenyl substituted dibenzoquinoxaline compounds, dithiophen-dibenzoquinoxaline compounds, and dibenzoquinoxaline compounds.

5 Claims, 23 Drawing Sheets

U.S. PATENT DOCUMENTS

| | | | |
|---|---|---|---|
| 6,259,204 B1 | 7/2001 | Ebisawa et al. | 313/512 |
| 6,262,433 B1 | 7/2001 | Arai et al. | 257/40 |
| 6,268,072 B1 | 7/2001 | Zheng et al. | 428/690 |
| 6,277,503 B1 | 8/2001 | Hashimoto et al. | 428/690 |
| 6,280,859 B1 | 8/2001 | Onikubo et al. | 428/690 |
| 6,303,239 B1 | 10/2001 | Arai et al. | 428/690 |
| 6,396,209 B1 * | 5/2002 | Kido et al. | 313/504 |
| 6,482,949 B1 * | 11/2002 | Sessler et al. | 544/343 |

* cited by examiner

XL 141 has good electron injection or transport ability.

Tm = 228°C; Td = 340°C; Characterized by GC-MAS, FT-IR, CV

Tm > 400°C; Td = 388°C,
Characterized by GC-
MAS, FT-IR, CV

ORGANIC LIGHT-EMITTING DEVICES

BACKGROUND OF THE INVENTION

1. Field of the Invention

The present invention relates generally to organic light-emitting devices, and to organic light-emitting compounds for use in such devices. In particular, the invention relates to organic light-emitting devices incorporating dibenzoquinoxaline derivatives.

2. Related Background Art

Electro-luminescent and electro-phosphorescent organic light-emitting devices ("OLEDs") are promising for flat-panel display applications. Successful commercialization of such flat-panel displays depends improvements in certain performance parameters, such as, e.g., efficiency, life-time, and color purity. Such improvements depend, in part, on the development of novel light-emitting materials. As OLEDs work through a double charge injection from two electrodes, i.e., holes are injected from the anode into the highest occupied molecular orbital (HOMO) of the hole transport layer molecules, and electrons from the cathode into the lowest unoccupied molecular orbital (LUMO) of the electron transport layer molecules, an improvement in the ability to inject charge in OLED materials has been an important approach in device development.

Essentially, a typical OLED comprises a transparent electrode of indium-titanium-oxide ("ITO") or other transparent electrode material formed on a glass substrate, an organic amine based hole transporting layer laminated onto the transparent electrode, an organic light emitting layer formed of a material having electronic conductivity and giving out strong light emission, e.g., tris(8-quinolinolato)aluminum complex ("AlQ$_3$"), and an electrode provided on the organic light emitting layer, formed from a material having a low work function, such as, e.g., an MgAg material. Typically, at least one organic compound layers is interleaved between a hole injecting electrode and an electron injecting electrode, and the organic compound layer has a double- or triple-layer structure.

In double-layer structures, a hole transporting layer and a light emitting layer are formed between the hole injecting electrode and the electron injecting electrode, or a light emitting layer and an electron transporting layer are formed between the hole injecting electrode and the electron injecting electrode. In triple-layer structures, a hole transporting layer, a light emitting layer and an electron transporting layer are provided between the hole injecting electrode and the electron injecting electrode.

In general, organic materials used in OLEDs have a higher barrier to electron injection at the cathode-organic layer interface and a lower electron mobility than do inorganic materials used in such devices. As a result, a charge injection imbalance between the holes and electrons and the charge density near the interface of the two organic layers may occur. Therefore, an improvement in electron injection ability, and the employment of an electron transporting layer in multi-layered devices can provide improved device work efficiency and lifetime. The luminescent properties and electron injection ability of AlQ$_3$ are both good, and, thus, AlQ$_3$ has been utilized in various high efficient OLED devices. However, as the peak emission of AlQ$_3$ is 526 nm, i.e., in the green portion of the visible spectrum, its application in blue and red devices is limited. As a result, wider band gap materials would be more desirable than AlQ$_3$, and a need exists for electron-transporting materials having a band gap covering the entire visible spectrum from purple to red.

U.S. Pat. No. 6,303,239 to Arai, et al. discloses an organic electro-luminescent device, comprising a substrate, a pair of a hole injecting electrode and a cathode formed on said substrate, and an organic layer located between these electrodes, which, at least in part, performs the light emission function. An inorganic insulating electron injecting and transporting layer is provided between the organic layer and the cathode. The inorganic insulating electron injecting and transporting layer comprises a first component comprising at least one oxide selected from the group consisting of lithium oxide, rubidium oxide, potassium oxide, sodium oxide and cesium oxide, a second component comprising at least one oxide selected from the group consisting of strontium oxide, magnesium oxide and calcium oxide, and a third component comprising silicon oxide and/or germanium oxide. The disclosed light emitting layer contains a fluorescent material in combination with a host substance capable of emitting light by itself; i.e., the fluorescent compound is used as a dopant. Quinolinolato complexes, and aluminum complexes containing 8-quinolinol or its derivatives as ligands are disclosed as the host substance.

U.S. Pat. No. 6,277,503 to Hashimoto, et al. discloses an organic electroluminescent component, comprising an aromatic methylidene compound of the general formula

where the various Ar groups are substituted or unsubstituted aromatic groups, and n is 1 to 6. The construction of the organic electroluminescent component is typically a luminescent layer interposed between a pair of electrodes, i.e., a cathode and an anode, and may further comprise a positive hole-transporting layer and an electron-transporting layer.

U.S. Pat. No. 5,861,219 to Thompson, et al. discloses organic light emitting devices containing a metal complex of 5-hydroxy-quinoxaline as a host material. The disclosed organic light emitting devices have an electroluminescent layer containing a host material comprising a metal complex of (5-hydroxy)quinoxaline and a dopant material comprising at least one of a bisphenyl-squarilium compound, an indigo dye compound and a fullerene compound.

U.S. Pat. Nos. 6,245,449 and 6,150,042 to Tamano, et al. disclose a hole-injecting material, having a triphenylene structure, for an organic electro-luminescent device and an organic electro-luminescent device using the disclosed hole-injecting material. The disclosed organic electroluminescence device comprises a light-emitting layer or a plurality of organic compound thin layers including the light-emitting layer between a pair of electrodes composed of a cathode and an anode, where at least one layer contains the disclosed hole-injecting material.

U.S. Pat. No. 6,255,449 to Woo, et al. discloses 2,7-dihalofluorenes, substituted at the 9-position, methods for the preparation of such 9-substituted-2,7-dihalofluorenes, oligomers and polymers of the disclosed fluorine compounds, films and coatings prepared from such florins, oligomers and polymers, processes for preparing such films and coatings, and light-emitting diodes comprising one or more layers of the polymer films, where at least one of the layers is derived from the oligomers and polymers of the invention.

U.S. Pat. No. 6,268,072 to Zheng, et al. discloses an electroluminescent device comprising an anode, a cathode, and polymer luminescent materials disposed between the anode and cathode, where the disclosed polymeric luminescent materials are 9-(4-adamantanyl)phenyl)-10-phenylanthracene-based polymers.

U.S. Pat. No. 5,792,567 to Kido, et al. discloses organic electroluminescent devices having a layer comprising at least one triazole derivative. Preferably, the layer is an electron-transport layer containing the oligomerized triazole derivatives as an electron-transport material.

U.S. Pat. No. 5,904,994 to Dodabalapur, et al. discloses blue emitting materials, which, when placed in electroluminescent devices with an emitter layer and a hole transporter layer, provide white light. The disclosed materials are non-polymerizable. i.e., containing no ethylenic unsaturation, and contain at least one unsaturated, five or six-membered heterocyclic moiety with at least one nitrogen atom incorporated into the heterocycle. These moieties are incorporated into molecules that form amorphous films when deposited using conventional techniques such as vacuum sublimation. The moieties are selected from the group consisting of oxazole, imidazole, quinoline, and pyrazine.

There is no known prior art disclosure of organic light-emitting devices utilizing the advantageous properties of the dibenzoquinoxaline derivatives discussed below. The present invention provides such organic light-emitting devices.

SUMMARY OF THE INVENTION

The present invention is directed to electron transporting materials and organic light emitting devices comprising the electron transporting materials, wherein the electron transporting materials are dibenzoquinoxaline compounds, and the devices comprise at least one layer comprising at least one dibenzoquinoxaline compound. Dibenzoquinoxaline compounds of the invention include dipyridyl substituted dibenzoquinoxaline compounds, diphenyl substituted dibenzoquinoxaline compounds, naphthalene substituted dibenzoquinoxaline compounds, anthrene-dibeanzoquinoxaline compounds, bis(methoxy)phenyl substituted dibenzoquinoxaline compounds, dithiophen-dibenzoquinoxaline compounds, and dibenzoquinoxaline compounds. Preferably, the at least one dibenzoquinoxaline compound is present in the electron transporting material or the at least one layer in an amount of at least about 1 percent by weight.

DETAILED DESCRIPTION OF THE PREFERRED EMBODIMENTS

The present invention is directed to electron transporting materials and organic light emitting devices comprising the electron transporting materials, wherein the electron transporting materials are dibenzoquinoxaline compounds. Preferably, the dibenzoquinoxaline compounds are dibenzoquinoxaline derivative of the general formula (I)

(I), where n=1 to 12, X and Y are independently H, alkyl, alkoxy, aryl, heteroaryl, fused aryl, fused heteroaryl, fused aryl with functional groups, fused heteroaryls with functional groups, etc. when n is 1, and X and Y are independently aryl or heteroaryl rings, fused or lined aromatic chromophores thereof, including $C_{60}$ et al. when n is greater than 1, and to organic light-emitting devices having at least one layer comprising at least one dibenzoquinoxaline derivative of the general formula (I).

Organic light-emitting devices in accordance with the invention preferably comprise a plurality of layers, where at least one of the layers comprises at least one dibenzoquinoxaline derivative of formula (I). For example, in a three layer organic light-emitting device, which preferably comprises an electron-transporting layer, an emissive layer, and a hole-transporting layer, sandwiched between a pair of electrodes (i.e., an anode and cathode), at least one of the electron-transporting layer, the emissive layer, and the hole-transporting layer, contains at least one dibenzoquinoxaline compound, preferably a dibenzoquinoxaline derivative of formula (I). Organic light-emitting devices in accordance with the invention contain at least one dibenzoquinoxaline derivative in an electron-transporting layer (ETL), as a host material, or as a dopant emissive material, as a hole blocking layer, or as a exciton blocking layer. Organic light-emitting devices in accordance with the invention are particularly useful in flat-panel displays.

When n is greater than 1 in dibenzoquinoxaline derivatives of formula (I), the resulting branched or star-burst structures of formula (II) and formula (III) make the organic semiconductor more difficult to recrystalize.

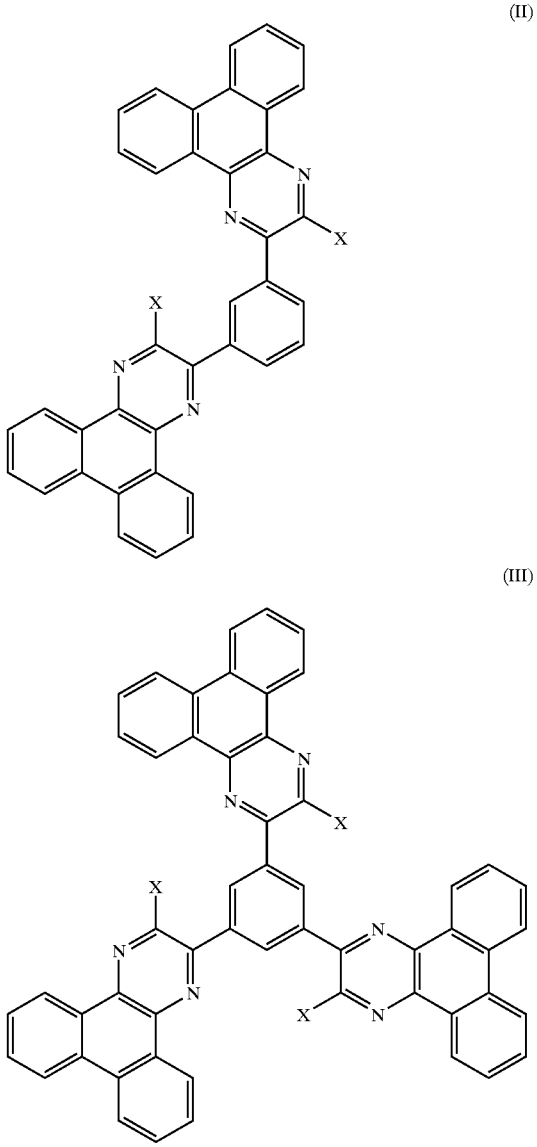

However, the thin film of the side material provided via solution coating or thermal vacuum deposition methods has improved uniformity and, thus, improved performance of thin film devices, such as organic light-emitting device.

EXAMPLES

The following non-limiting examples are merely illustrative of the preferred embodiments of the inventory and are not to be construed as limiting the invention, the scope of which is defined by the appended claims.

Aromatic quinoxaline compounds have the characteristics of high electron affinity as well as good luminescent properties. A series of dibenzoquinoxaline compounds have been developed as electron transport materials, emissive materials, and host materials.

Example 1

Figure 1:
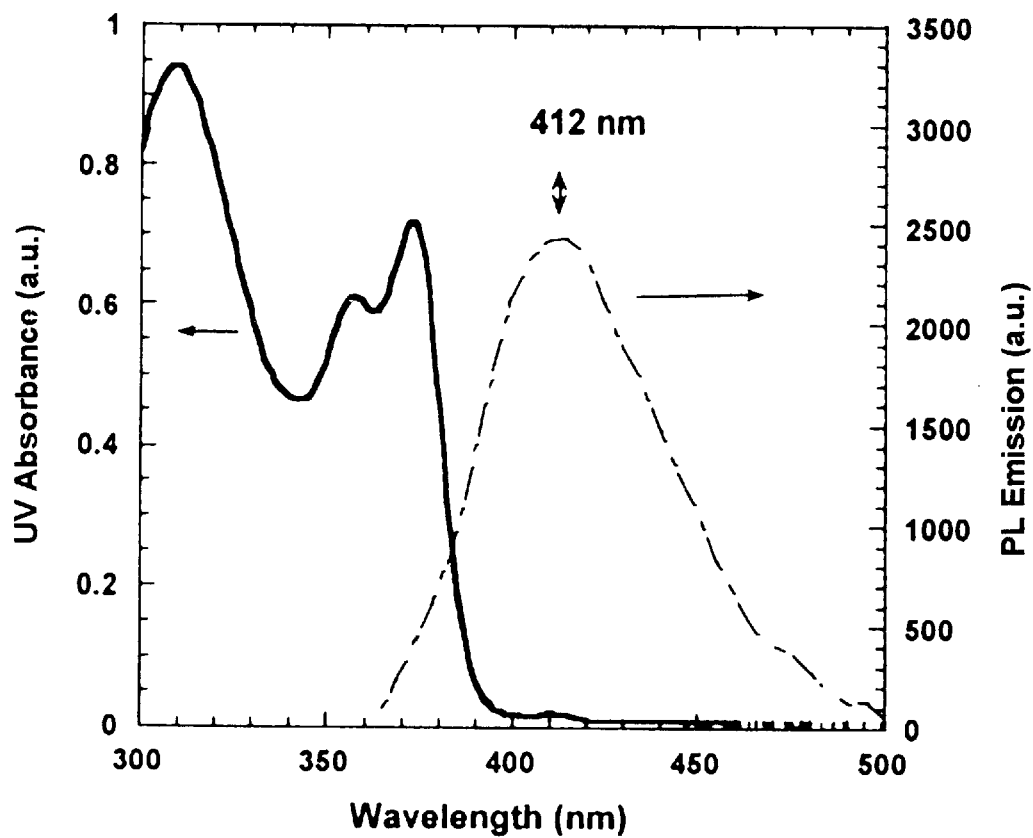
FIG. 1 illustrates the UV-visible and photoluminescence spectra of dipyridyl substituted dibenzoquinoxaline.

A dipyridyl substituted dibenzoquinoxaline compound, 2,3-di-pyridin-2-yl-dibenzoquinoxaline, was prepared with a yield of 89 percent using Scheme 1, provided below. The white crystal compound fluoresces purple under UV irradiation. The UV-visible and photoluminescence spectra of the compound in dichloromethane solution are shown in FIG. 1.

Scheme 1.
Synthesis of dipyridyl substituted dibenzoquinoxaline

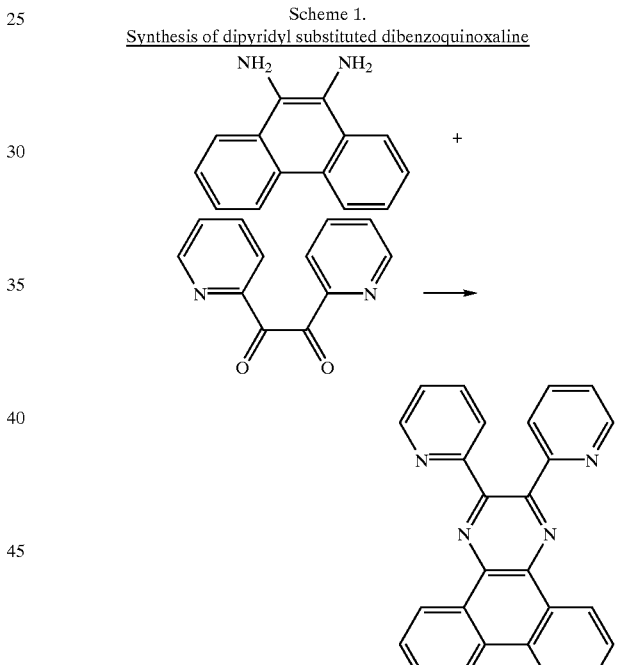

Figure 2:
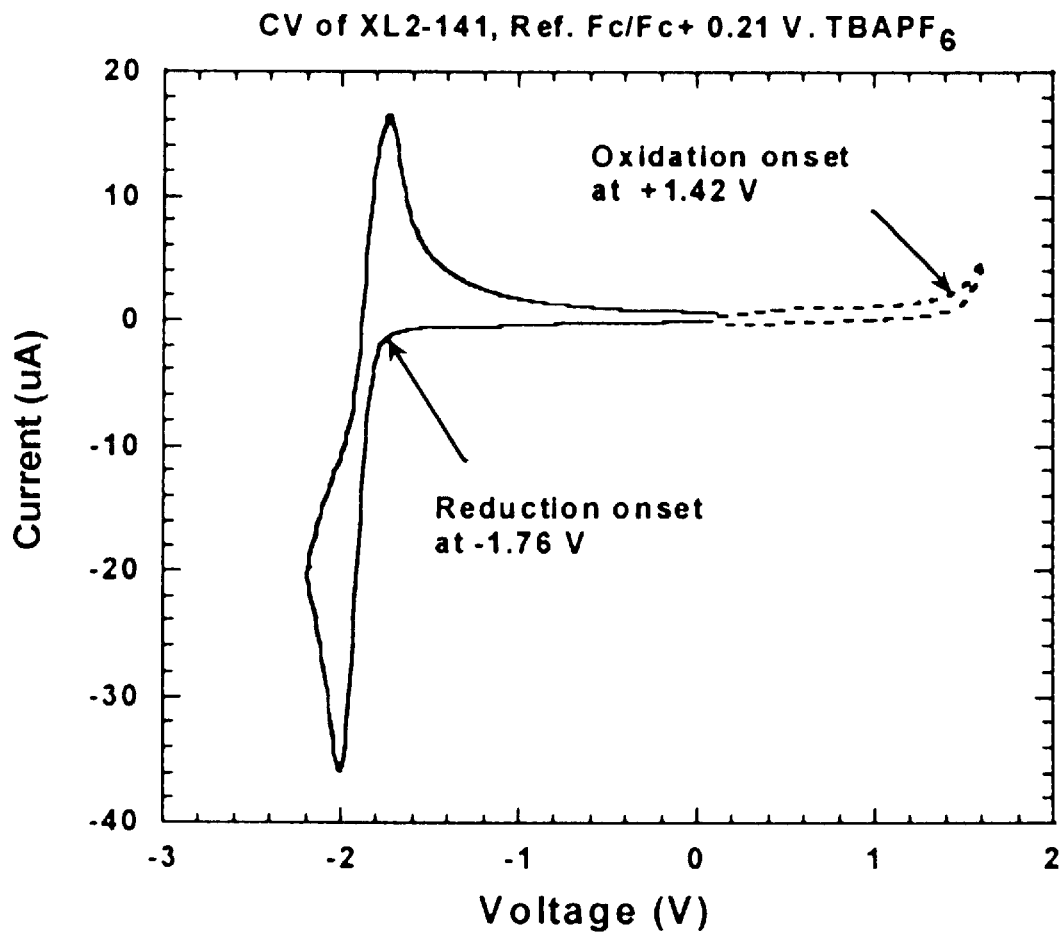
FIG. 2 illustrates the cyclic voltametric analysis of dipyridyl-dibenzoquinoxaline.

Cyclic voltametric analysis demonstrates that the compound has excellent electron injection and hole blocking properties, which are illustrated in FIG. 2. The HOMO, LUMO level of the compound is 3.0 eV and 6.2 eV respectively as estimated by the cyclic voltametric analysis.

Example 2

Figure 3:
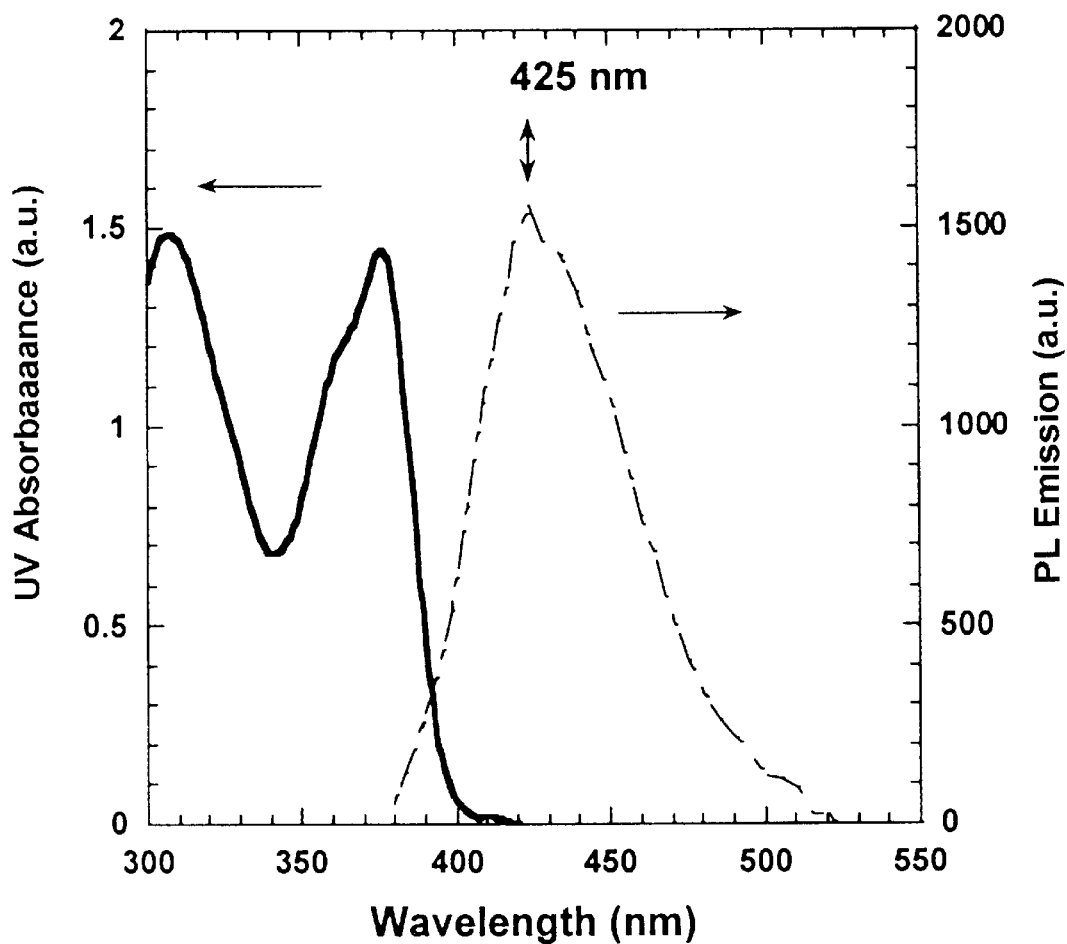
FIG. 3 illustrates the UV-visible and photoluminescence spectra of a diphenyl substituted dibenzoquinoxaline in dichloromethane solution.

Using a similar chemistry, a diphenyl substituted dibenzoquinoxaline compound, 2,3-di-phenyl-dibenzoquinoxaline, was also prepared with a yield of 92 percent, as illustrated in Scheme 2. The white crystalline compound fluoresces purple-blue under UV irradiation. FIG. 3 illustrates the UV-visible and photoluminescence spectra of the compound.

Scheme 2.
Synthesis of diphenyl substituted dibenzoquinoxaline

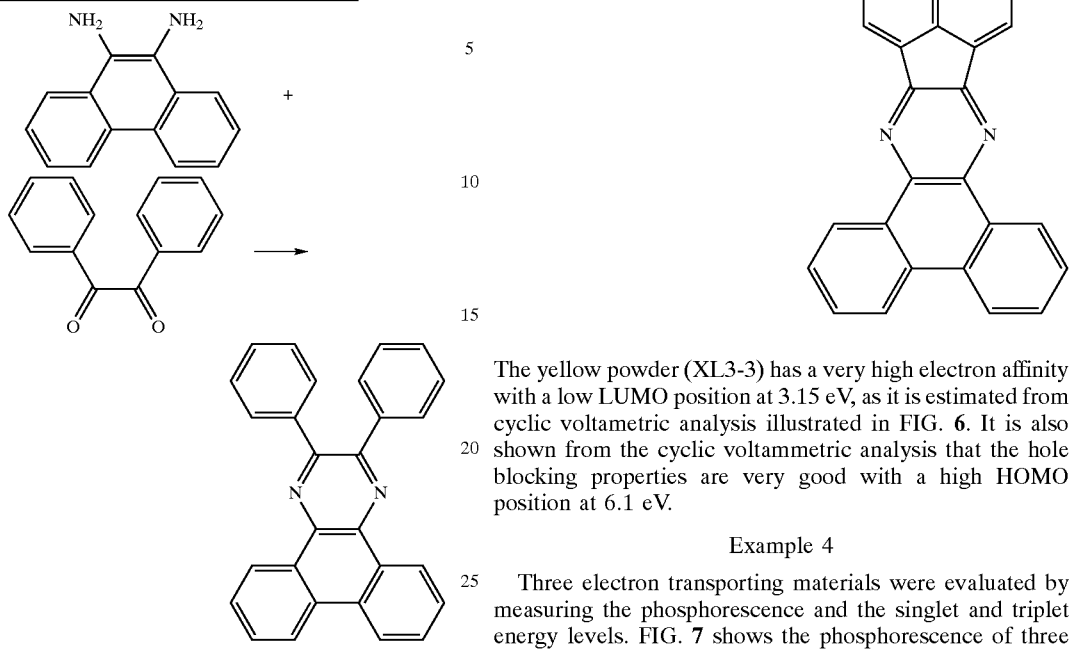

Figure 4:
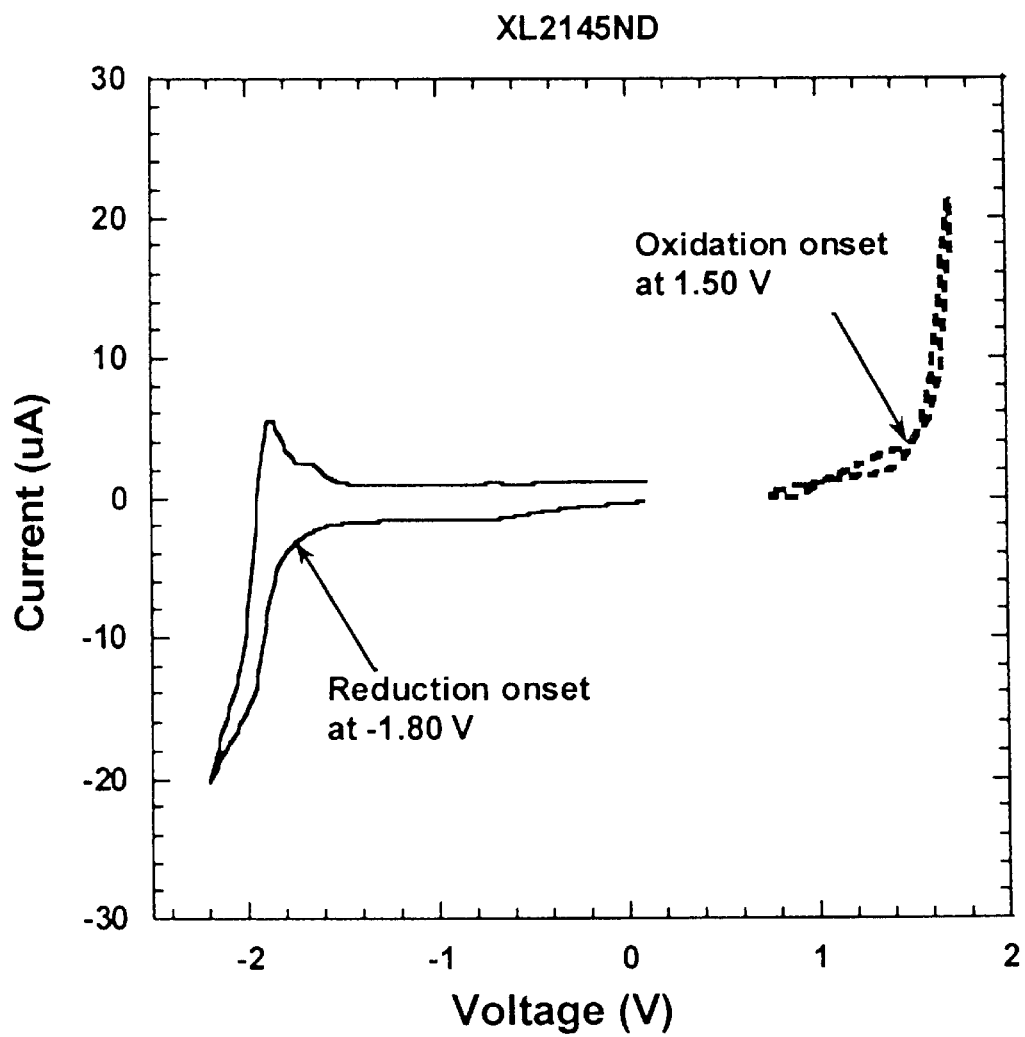
FIG. 4 illustrates the cyclic voltametric analysis of diphenyl dibenzoquinoxaline.

The diphenyl substituted dibenzoquinoxaline has a high electron affinity with a low LUMO level (3.0 eV) as estimated by cyclic voltametric analysis, the results of which are illustrated in FIG. 4. The band gap of 3.1 eV is slightly lower than that of the dipyridyl dibenzoquinoxaline.

Example 3

Figure 5:
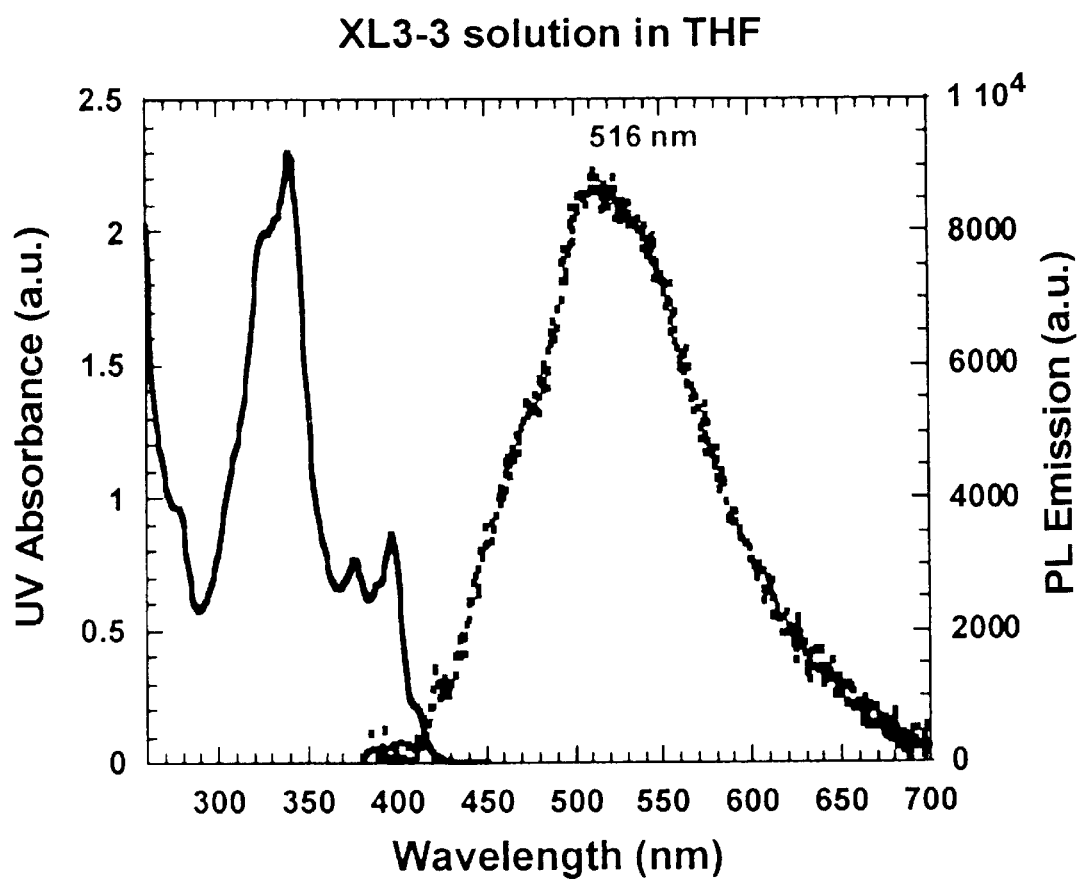
FIG. 5 illustrates the UV-visible and photoluminescence spectra of a naphthalene dibenzoquinoxaline compound.

A naphthalene dibenzoquinoxaline was prepared according to Scheme 3. The compound has thermal stability with a melting temperature of as high as 354° C. and a thermal decomposition temperature of 360° C., i.e., a 5 percent weight loss during thermal gravimetric analysis. The compound in the form of a yellow powder fluoresced green in solution. FIG. 5 shows the UV-visible and photoluminescence spectra in tetrahydrofuran.

Scheme 3.
The synthesis of naphthalene dibenzoquinoxaline (XL3-3)

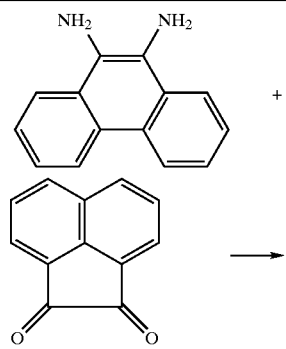

-continued

Figure 6:
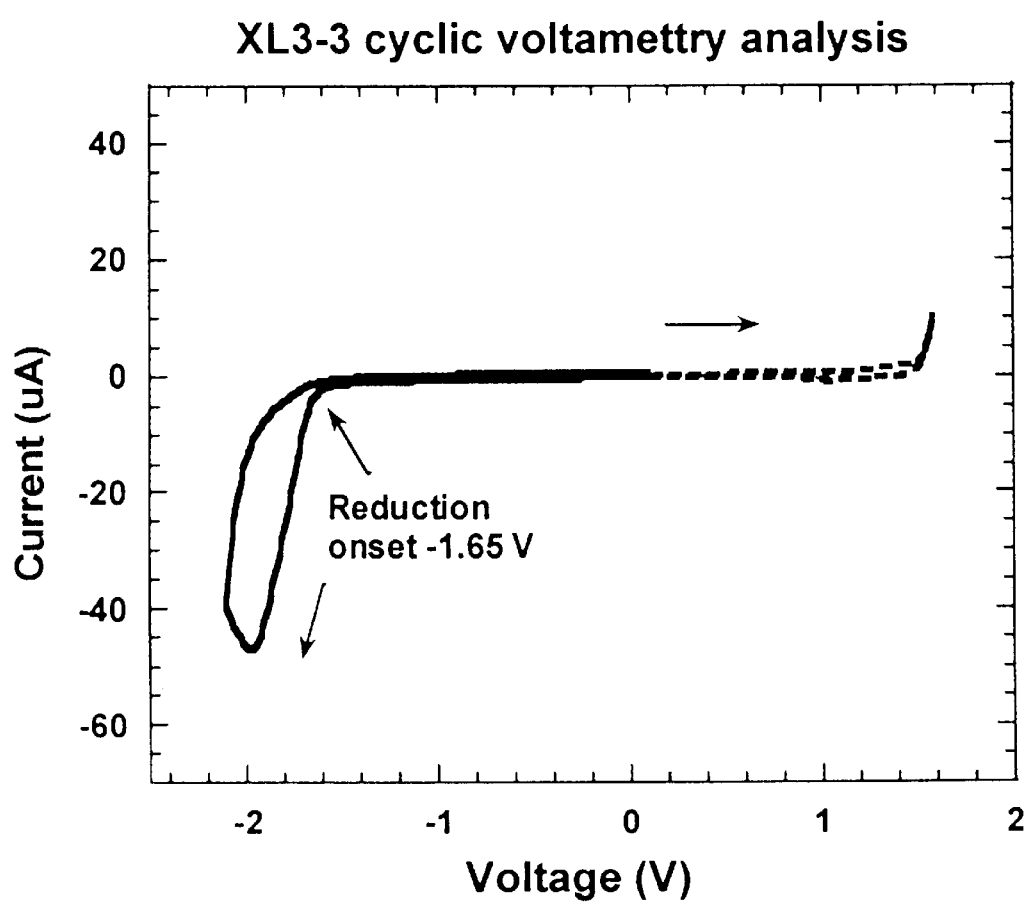
FIG. 6 illustrates the cyclic voltametric analysis of a naphthalene dibenzoquinoxaline.

The yellow powder (XL3-3) has a very high electron affinity with a low LUMO position at 3.15 eV, as it is estimated from cyclic voltametric analysis illustrated in FIG. 6. It is also shown from the cyclic voltammetric analysis that the hole blocking properties are very good with a high HOMO position at 6.1 eV.

Example 4

Figure 7:
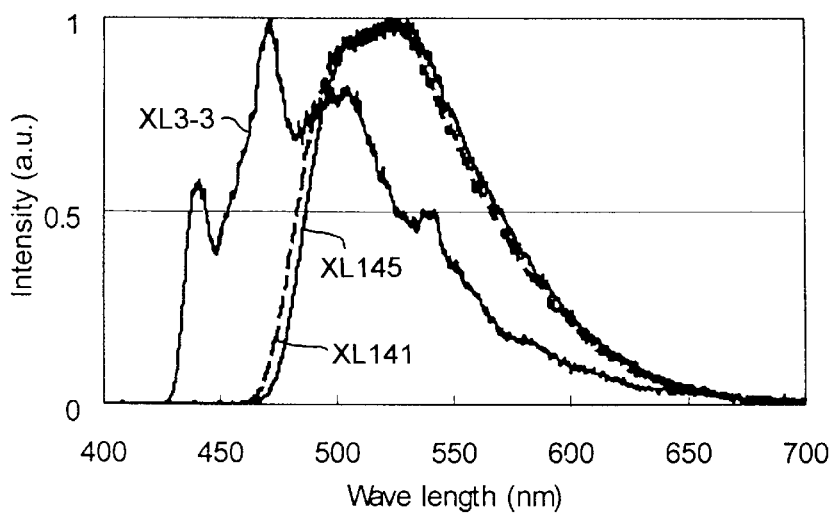
FIG. 7 is the phosphorescence spectra of the dipyridyl-dibenzoquinoxaline, diphenyl-dibenzoquinoxaline, and naphthalene-dibenzoquinoxaline.

Three electron transporting materials were evaluated by measuring the phosphorescence and the singlet and triplet energy levels. FIG. 7 shows the phosphorescence of three electron transporting quinoxaline compounds. Their corresponding energy levels of singlet and triplet were obtained from the phosphorescence. From the results illustrated in FIG. 7, it is clear that the dipyridyl-dibenzoquinoxaline (XL141) and diphenyl-dibenzoquinoxaline (XL145) compounds have sufficient energy to be used as the host material for red phosphorescence materials, and that naphthalene dibenzoquinoxaline (XL3-3) can be suitable for green and red phosphorescence host materials according to their triplet energy T1 levels.

Example 5

Figure 8:
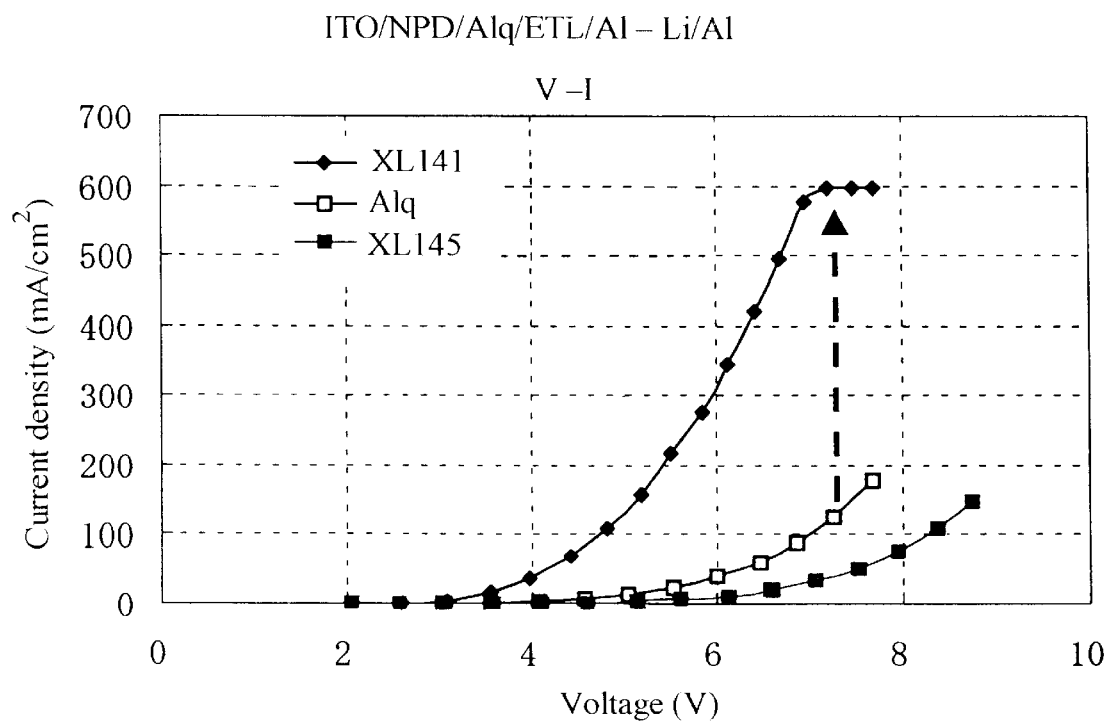
FIG. 8 illustrates the I-V curves of OLEDs using different electron transporting materials.

The dipyridyl-dibenzoquinoxaline compound was used as electron transporting material in a three layer ITO/α-NPD/ AlQ$_3$/ETL/Li—Al OLED and in a two layer ITO/α-NPD/ AlQ$_3$/Li—Al OLED without using an electron transporting layer, where ITO refers to indium tin oxide coated glass substrate used as the anode, α-NPD is N,N'-dinaphthlene-N,N'diphenyldiaminobiphenyl used for the 20 nm hole-transporting layer, AlQ$_3$ is a 50 nm layer of 8-hydroxyquinoline aluminum used as the emissive layer, and ETL is the electron-transporting layer having a thickness of 50 nm. It was found that dipyridyl dibenzoquinoxaline has a better electron transporting property than AlQ$_3$, as can be seen from FIG. 8. Clearly, XL141 is better than AlQ$_3$, and AlQ$_3$ is better than XL145. With the use of XL141, the OLED device has a lower turn-on voltage, and the current injection can be increased by more than a factor of 4.

Example 6

Figure 9:
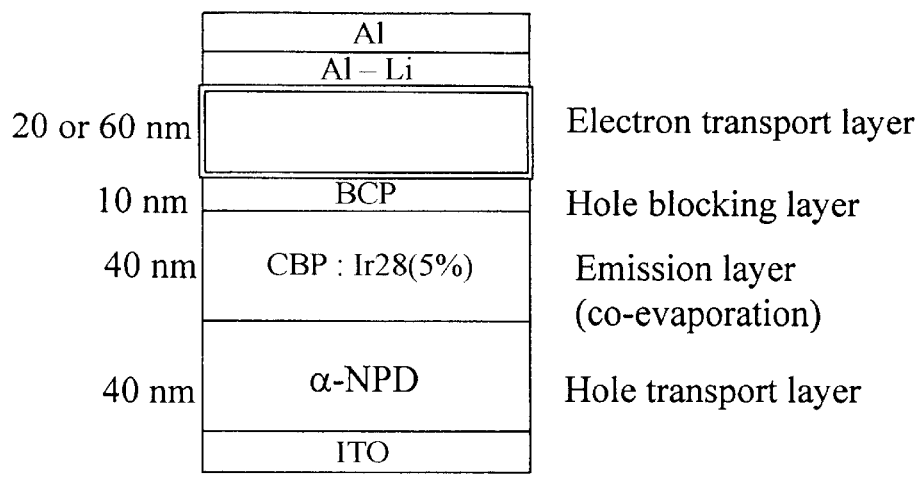
FIG. 9 illustrates a configuration of a four-layer triplet OLED device.

The electron transporting materials can be used in triplet OLEDs, as well as in singlet OLEDs. As illustrated in FIG. 9, a four-layer device was constructed by thermal vacuum evaporation method to evaluate electron transport materials. As illustrated in FIG. 9, CBP is a 4,4'-N,N'dicarbazole-biphenyl host material, Ir28 is fac tris(2-phenylpyridine iridium[Ir(ppy)$_3$], and BCP is a 2,9-dimethyl-4,7-diphenyl-1,10-phenynanthroline exciton layer.

Figure 10:
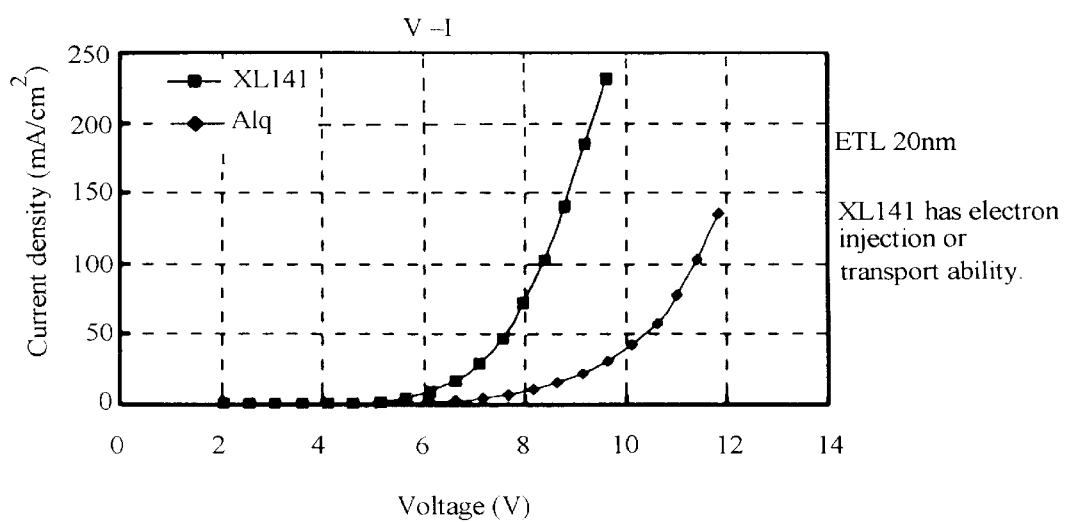
FIG. 10 illustrates the I-V-L curve of a four-layer triplet OLED using different electron transporting materials.

FIG. 10 shows that the dipyridyl-dibenzoquinoxaline has better electron injection and transporting properties than even AlQ₃. As a result, lower turn-on voltage and higher injection current can be achieved with the use of XL-141 as an electron injection layer.

Example 7

Figure 11:
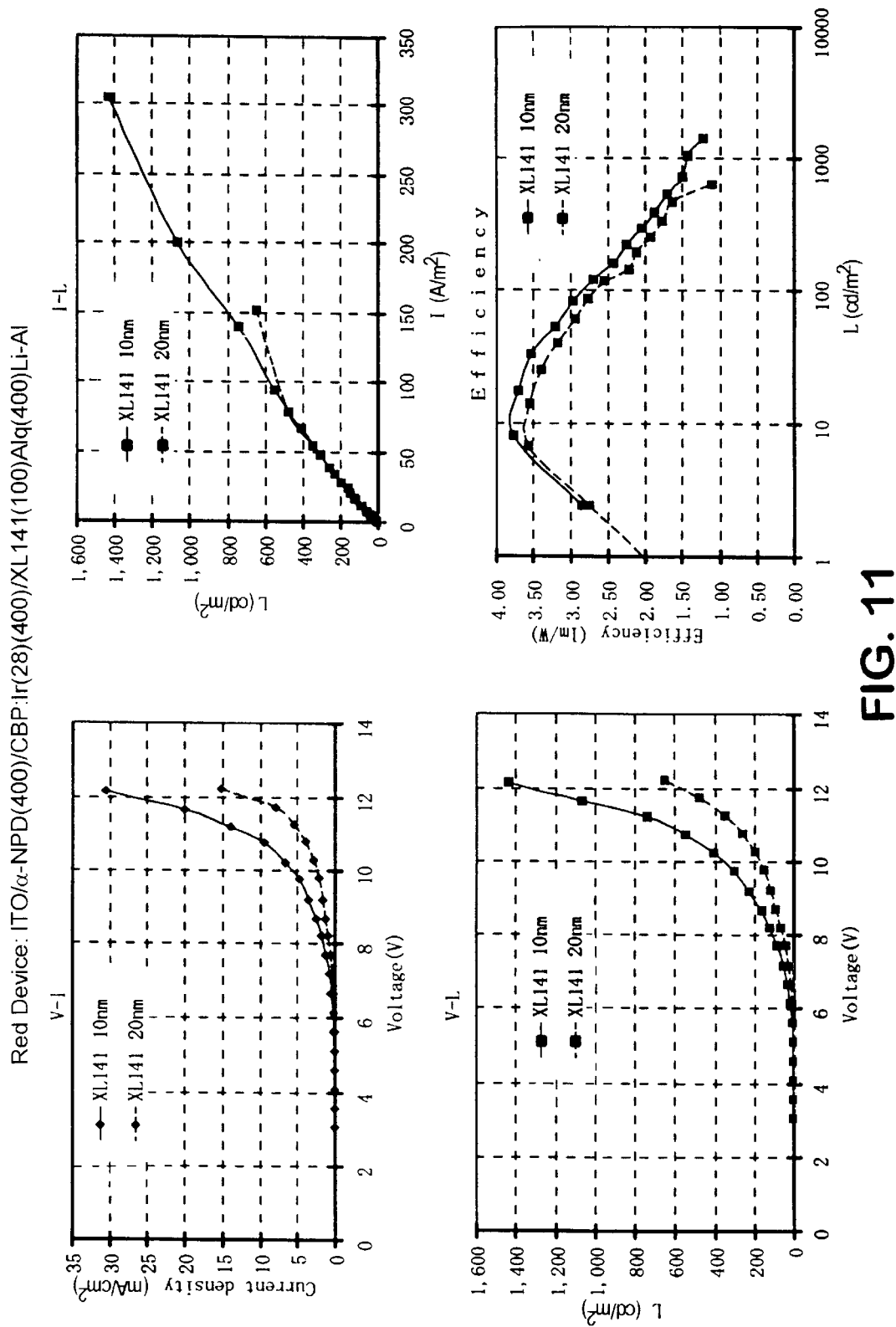
FIG. 11 illustrates the device characteristics of an OLED using dipyridyl-dibenzoquinoxaline as an exciton-blocking layer.
Figure 12:
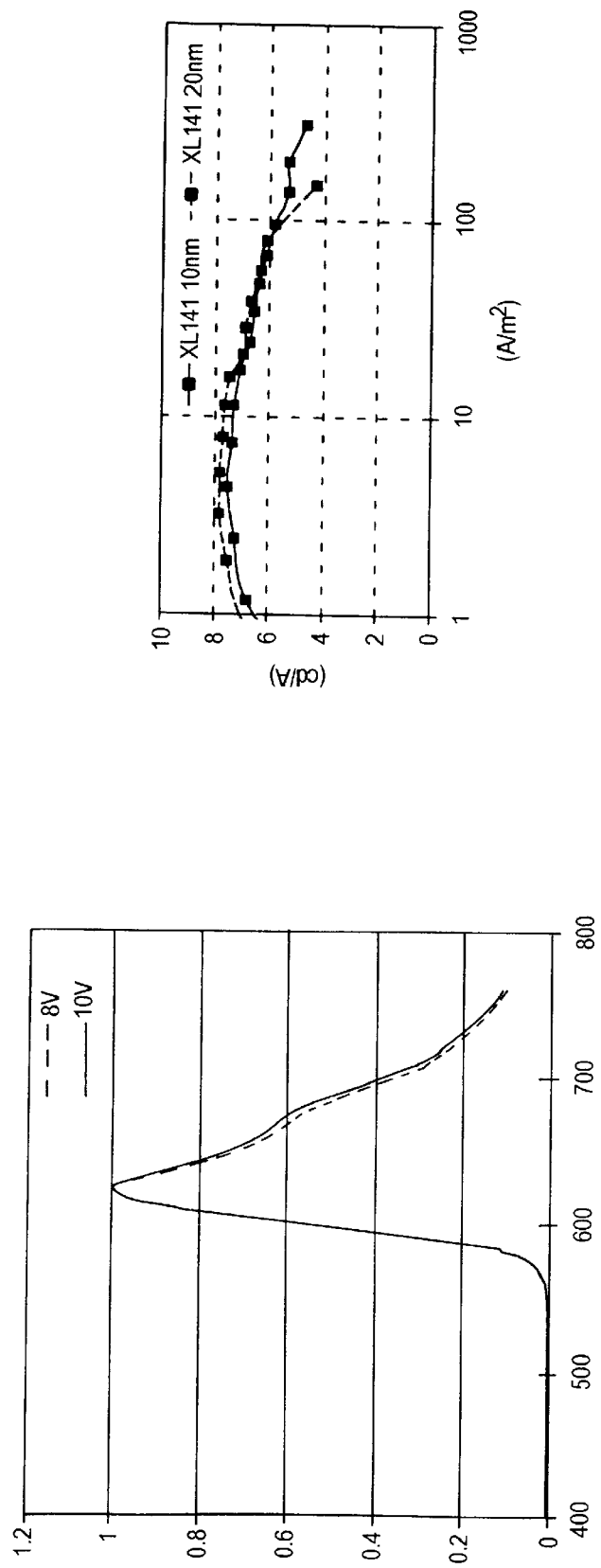
FIG. 12 illustrates the electroluminescence spectrum and electroluminenscence efficiency of a red OLED of the invention.

As the dipyridyl-dibenzoquinoxaline compound has both electron transporting and hole blocking properties, it can also be used as an exciton blocking layer in a triplet OLED. FIG. 11 shows the result of the OLED using XL-141 as the exciton blocking layer, rather than BCP. The optimal thickness of the exciton layer is about 10 nm, and, thus, a high luminance efficiency of 3.8 lm/W can be achieved for red a OLED. The electroluminenscence spectrum of such high performance red OLED is illustrated in FIG. 12, showing a really high efficiency of 8 cd/A with a spectral peak located at 618 nm.

Example 8

Chromophores with a dibenzoquinoxaline structure were engineered to function as both electron transporting and emissive materials. Scheme 4 shows the synthesis of anthrene-dibeanzoquinoxaline compound (XL2-135)

Scheme 4.
Synthesis of anthracene-dibenzoquinoxaline compound.

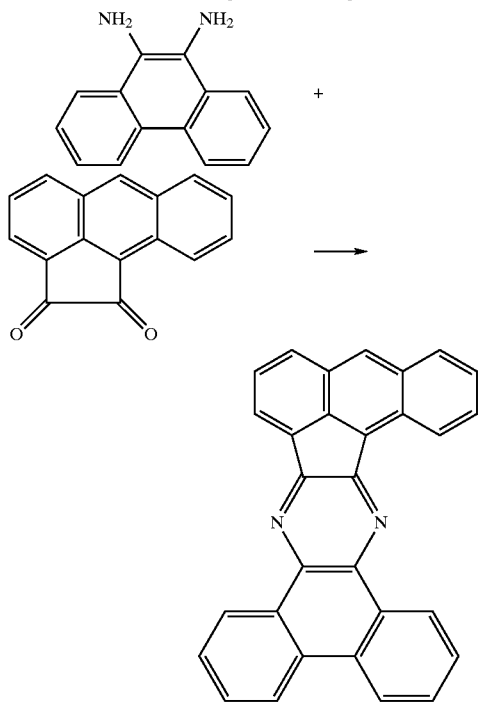

Figure 13:
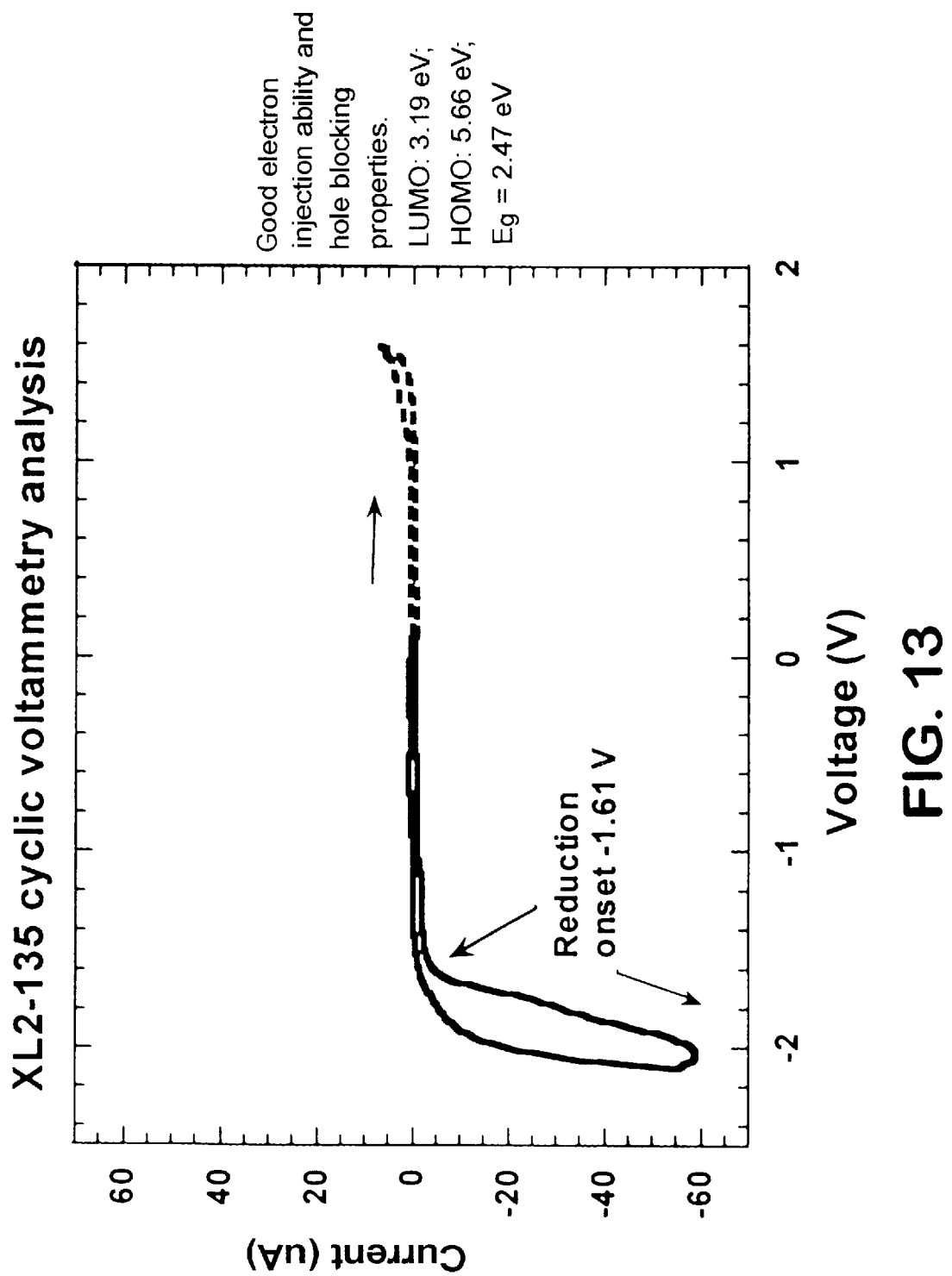
FIG. 13 illustrates the cyclic voltametric analysis of anthracene.
Figure 14:
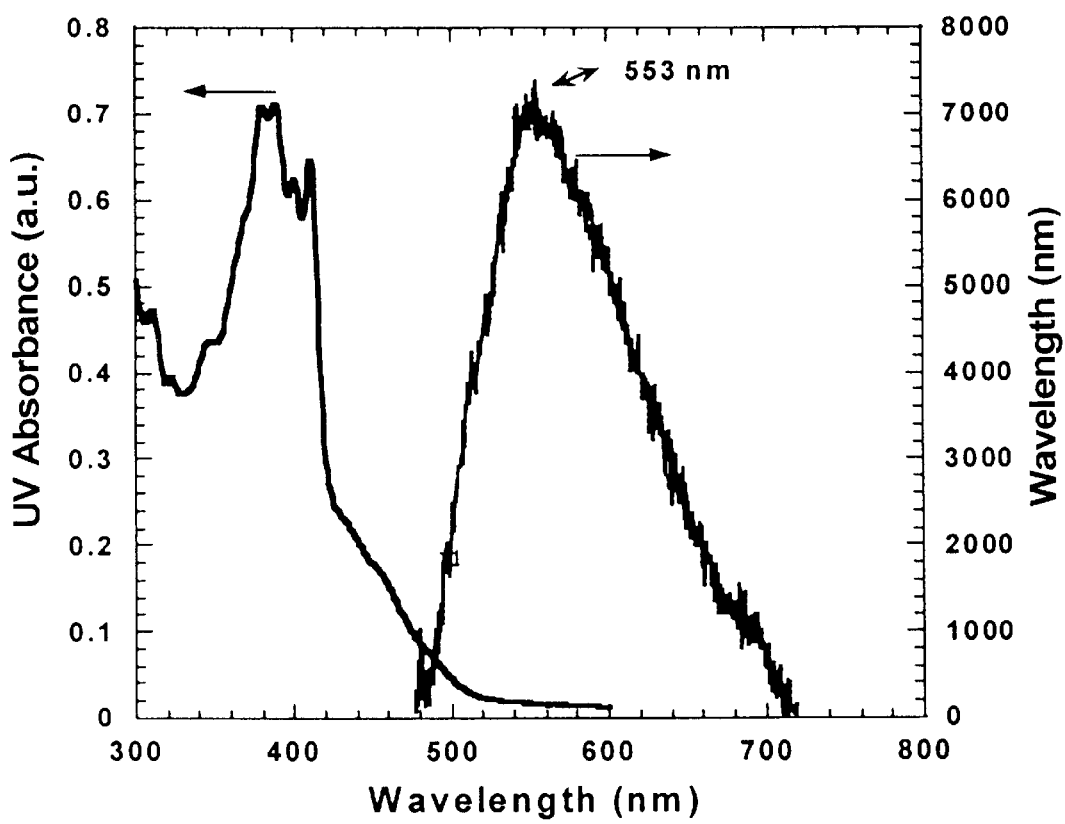
FIG. 14 illustrates the UV-Vis and photoluminescence spectra of an anthracene-dibenzoquinoxaline compound.

The compound anthracene-dibenzoquinoxaline (XL2-135) has good electron injection ability and hole blocking properties. It has a very low LUMO level of 3.19 eV, a HOMO of 5.66 eV, and an $E_g$=2.47 eV, as estimated from its cyclovoltametric analysis illustrated in FIG. 13, and, in solution, the compound fluoresces yellow as shown in FIG. 14.

Figure 15:
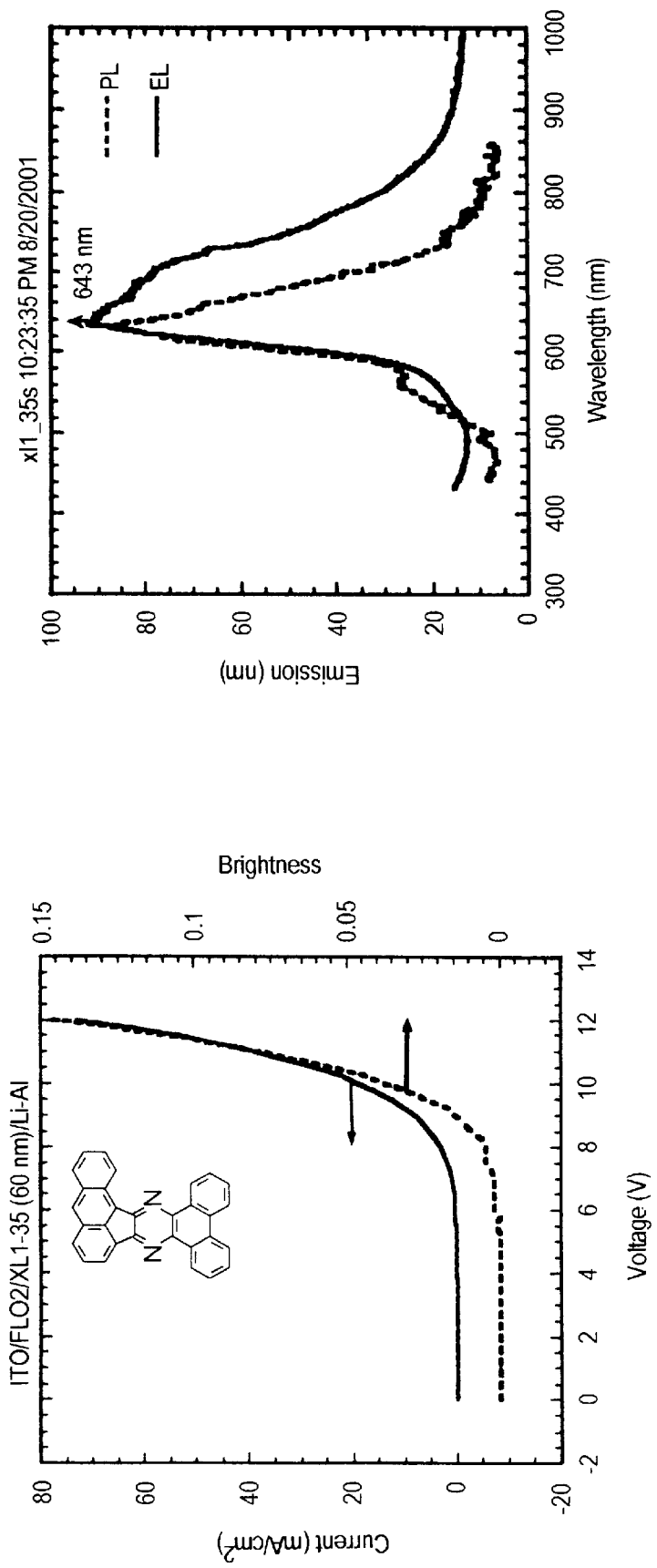
FIG. 15 illustrates the optical properties of an OLED of the invention.

As a solid powder or thin film, compound XL1-35, illustrated in FIG. 15 with the electroluminenscence spectrum of the compound, fluoresces red with an emission peak located at 630 nm. This compound is thus used as the red emissive layer. A ITO/HTL/XL1-35/Li—Al double layer device was fabricated, and gave red electroluminescence was observed when a forward bias voltage of about 8 volts was applied.

Figure 16:
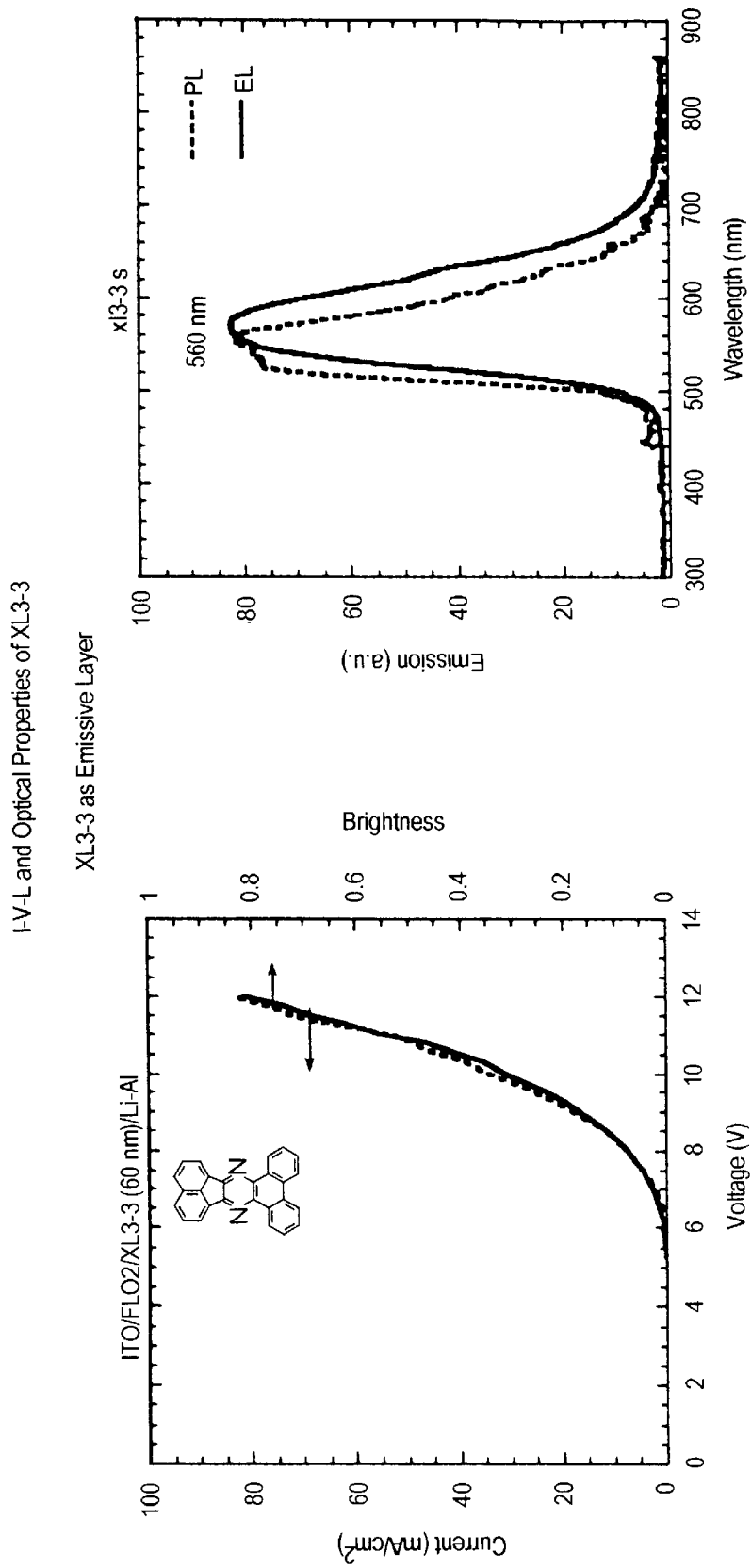
FIG. 16 illustrates the characteristics of an OLED of the invention.

Similarly, naphthalene-dibenzoquinoxaline was found to fluoresce orange with a solid state photoluminescence emission at 560 nm. When the material was used in a OLED of ITO/FL02 20 nm/XL3-3 60 nm/Li—Al, orange red electroluminescence was observed with the application of a forward bias voltage of ca. 8 V. The I-V-L relationship of the OLED device is provided in FIG. 16.

Example 9

Figure 17:
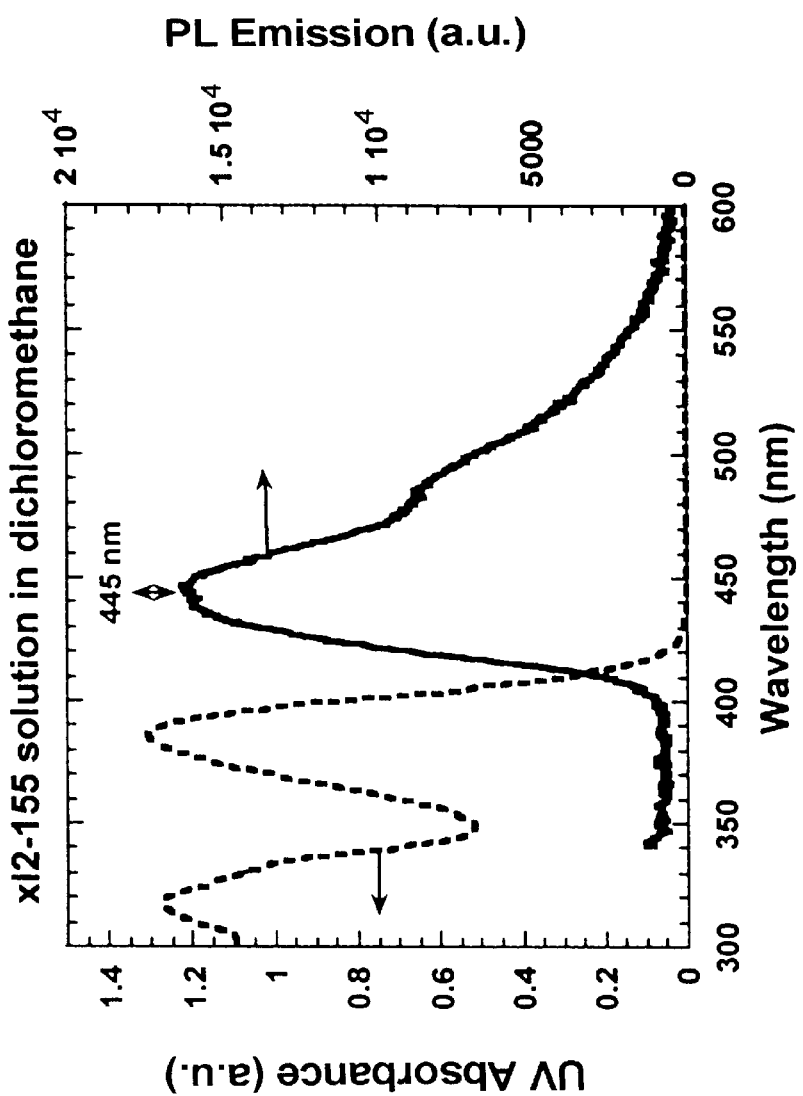
FIG. 17 illustrates the UV-visible and photoluminescence properties of a compound of the invention.
Figure 17:
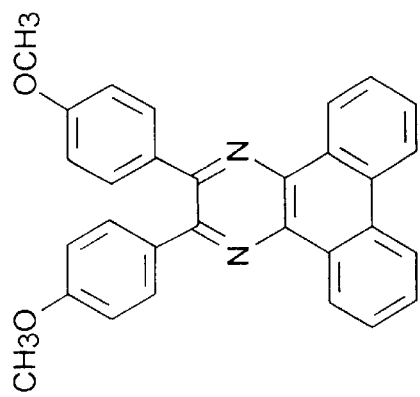

Other dibenzoquinoxaline compounds were prepared, and their optoelectronic properties were determined. To tune emission properties, various chromophores were designed and tested. As shown in FIG. 17, bis(methoxy)phenyl substituted dibenzoquinoxaline of the formula

Figure 18:
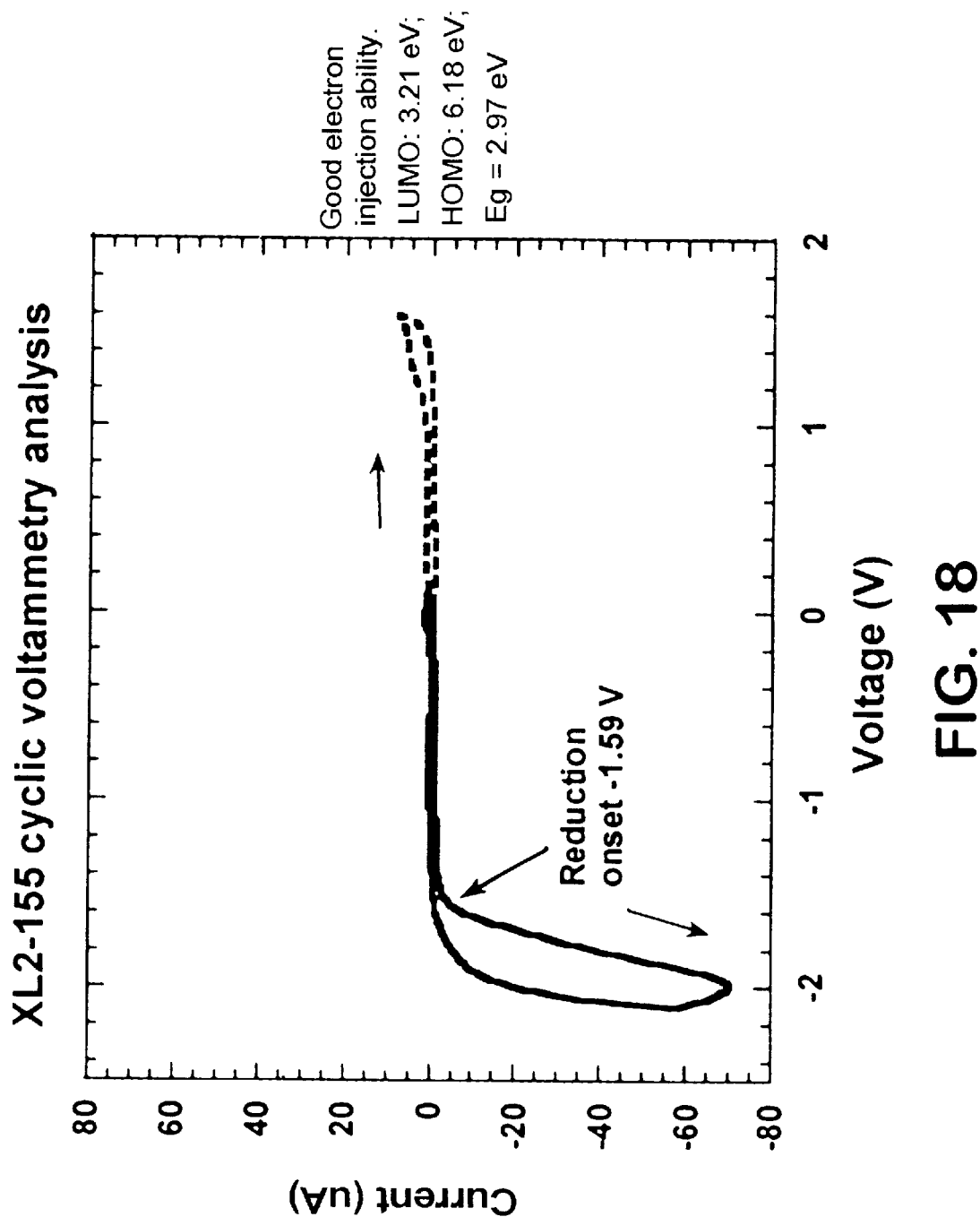
FIG. 18 illustrates the cyclic voltametric analysis of a compound of the invention.

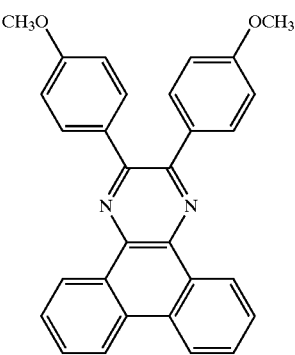

was prepared with a yield of 85 percent. The compound fluoresces blue in dichloromethane solution with a peak emission at 445 nm. The compound has a $T_m$=196° C., a $T_d$=320° C., and was characterized by GC-MAS, FT-IR, and cyclic voltammetric analysis. The results of the cyclic voltammetric analysis are provided in FIG. 18. The compound has a good electron injection ability, a LUMO of 3.21 eV, a HOMO of 6.18 eV, and an Eg=2.97 eV.

Figure 19:
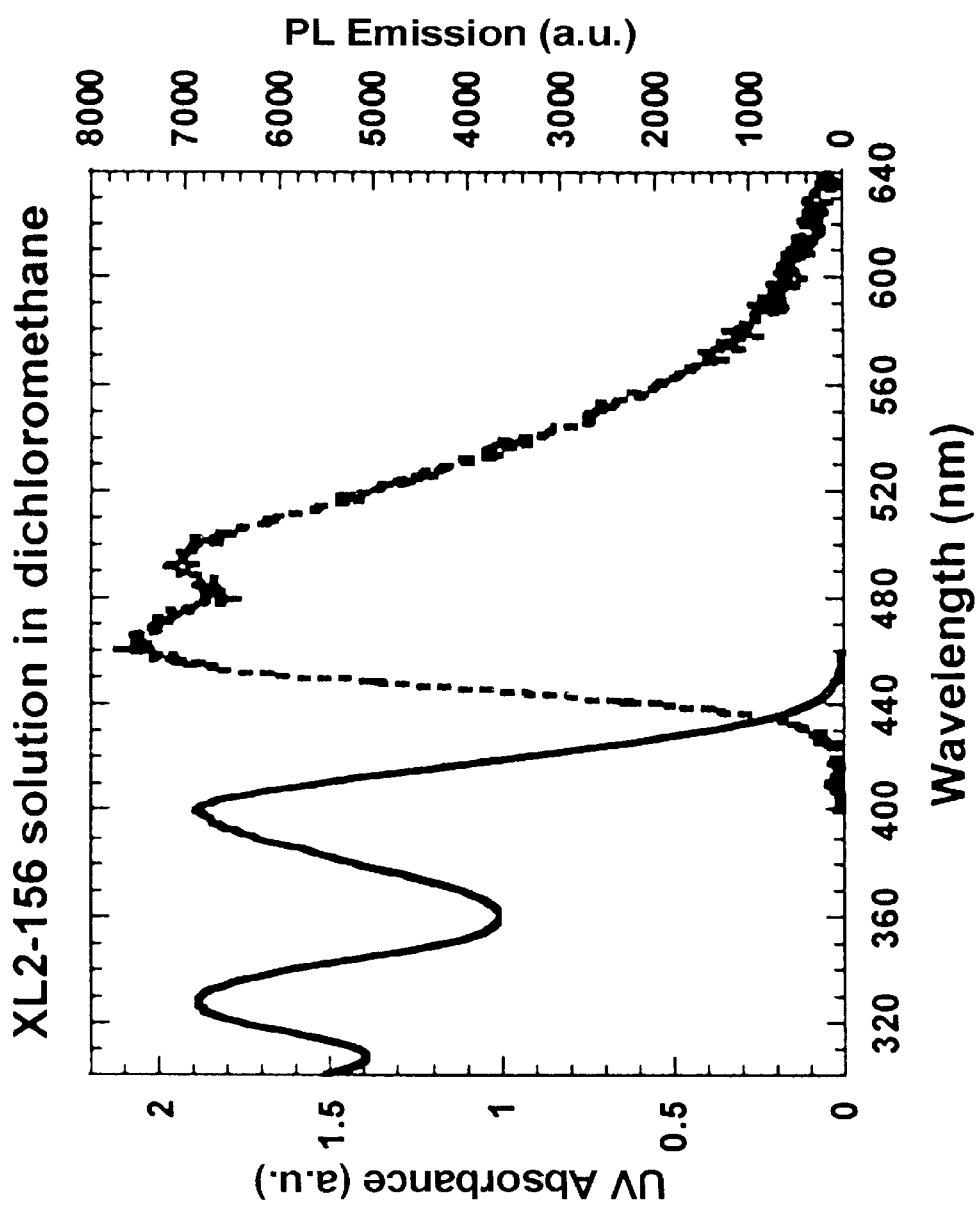
FIG. 19 illustrates the UV-visible and photoluminescence spectra of dithiophene-dibenzoquinoxaline in dichloromethane solution.
Figure 19:
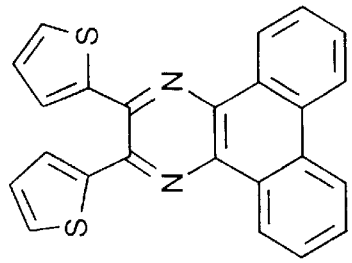
Figure 20:
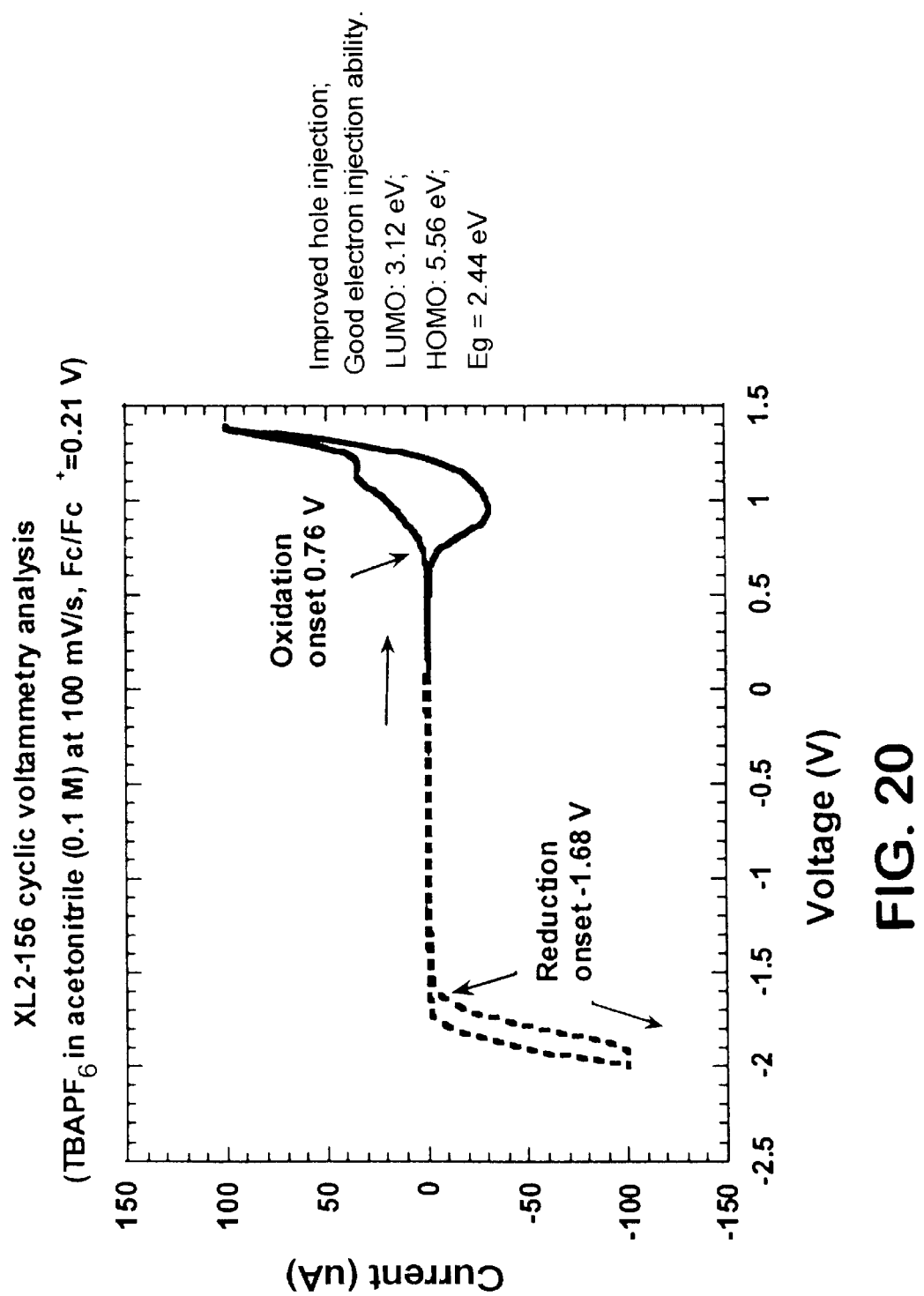
FIG. 20 provides the results of a cyclic voltametric analysis of dithiophene-dibenzoquinoxaline.

When thiophene rings are used to construct a dithiophen-dibenzoquinoxaline (XL2-156), the red powder fluoresces blueish green under UV irradiation. The UV-visible and photoluminescence spectra of the compound are shown in FIG. 19. The formula for the dithiophen-dibenzoquinoxaline compound is given below.

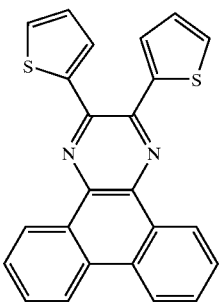

Figure 21:
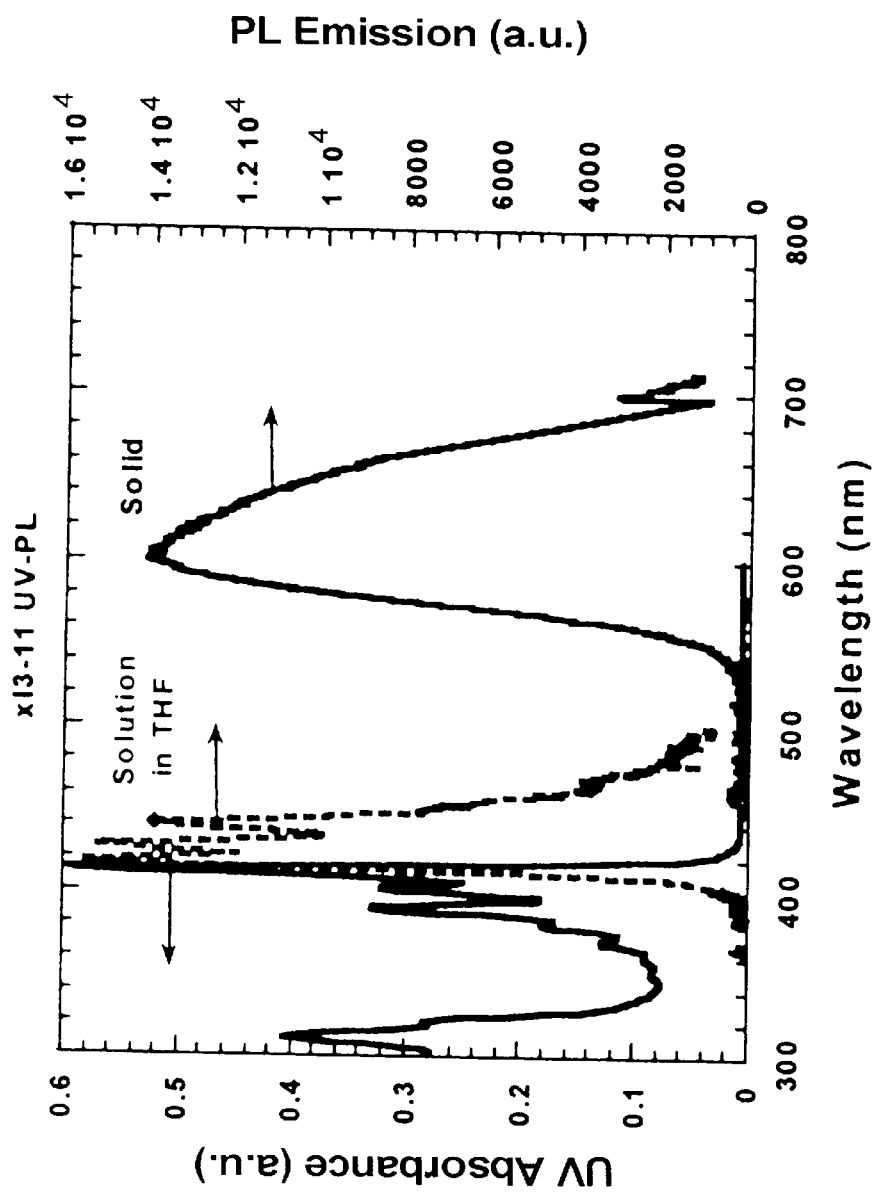
FIG. 21 illustrates the UV-visible and photoluminescence spectra of a symmetric dibenzoquinoxaline in solution and as a solid powder.
Figure 21:
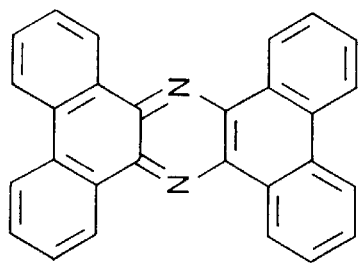

The compound has a $T_m$=228° C., a $T_d$=340° C., and was characterized by GC-MAS, FT-IR, and cyclic voltametric analysis. The cyclic voltametric analysis of the dithiophene-dibenzoquinoxaline compound indicates good hole injection properties, as shown in FIG. 21, which results from the thiophene substitution. Therefore, XL2-156 has both good electron and hole injection properties, a LUMO of 3.12 eV, a HOMO of 5.56 eV, and an Eg=2.44 eV.

A symmetric dibenzoquinoxaline compound (XL3-11) has also been prepared in a yield greater than 80 percent. The orange color powder fluoresces orange-red under UV irradiation. In THF solution, it provides photoluminescence spectrum is in blue range, as shown in FIG. 21. The structure of the symmetric dibenzoquinoxaline compound is shown below.

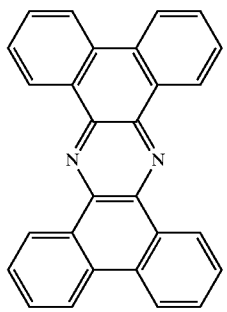

Figure 22:
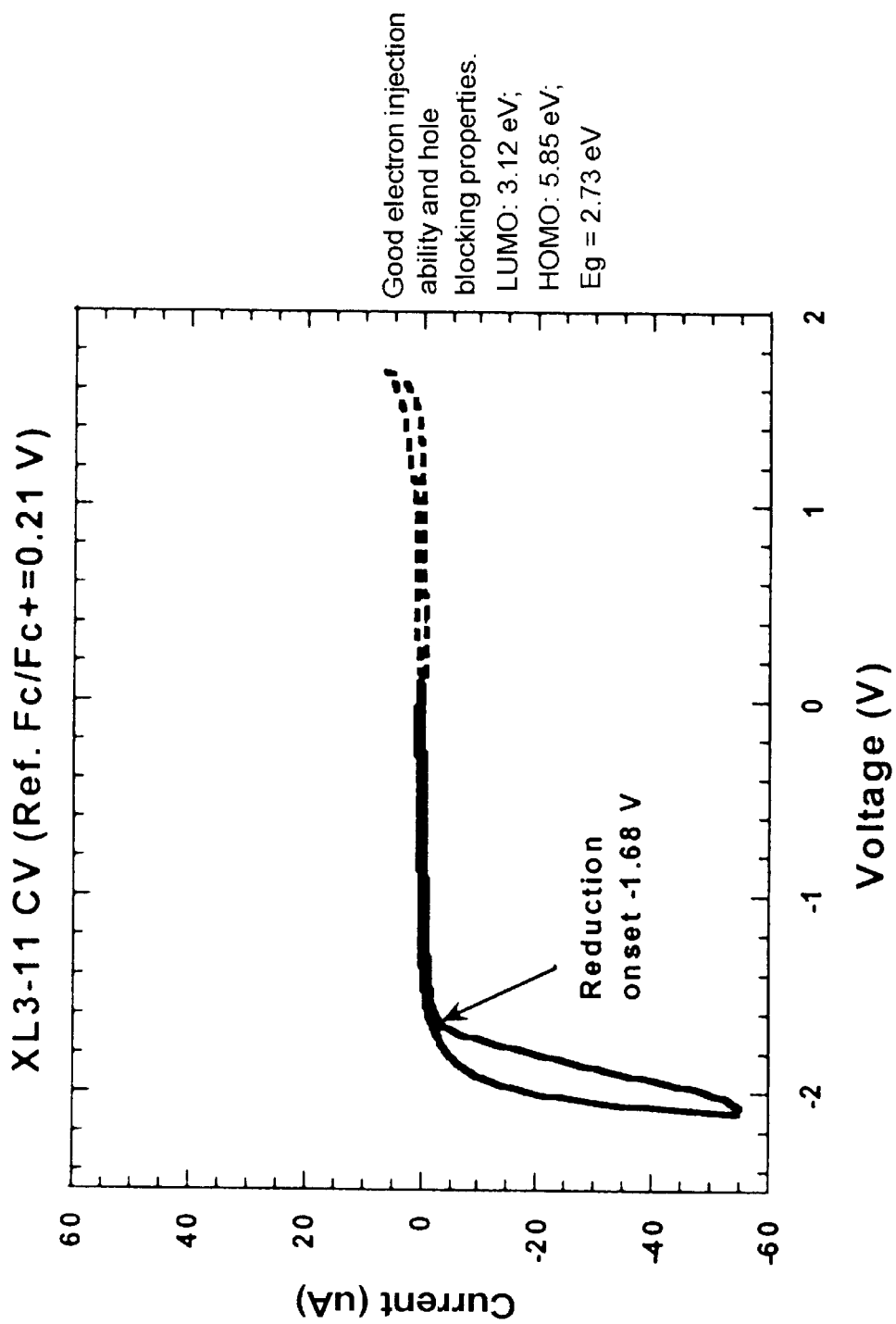
FIG. 22 illustrates the results of a cyclic voltametric analysis of the symmetric dibenzoquinoxaline.

The compound has a $T_m$ greater than 400° C., a $T_d$=388° C., and was characterized by GC-MAS, FT-IR, and cyclic voltammetric analysis. The results of a cyclic voltametric analysis of the symmetric dibenzoquinoxaline compound (XL3-11) is shown in FIG. 22, and indicate good electron injection and hole blocking properties, a LUMO of 3.12 eV, a HOMO of 5.85 eV, and an Eg=2.73 eV.

Example 10

Figure 23:
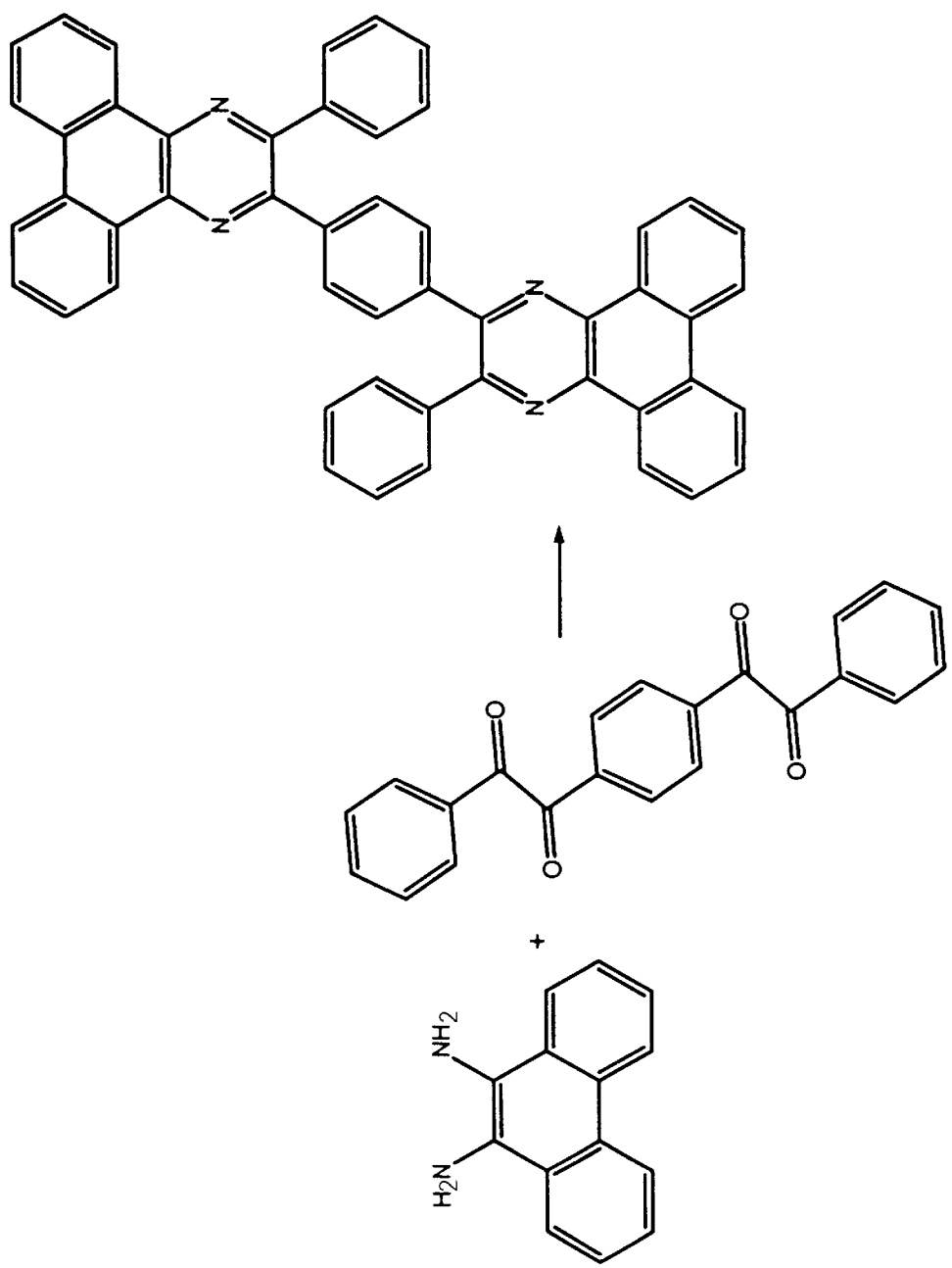
FIG. 23 illustrates a reaction scheme for the preparation of a dimer of dibenzoquinoxaline.
Figure 24:
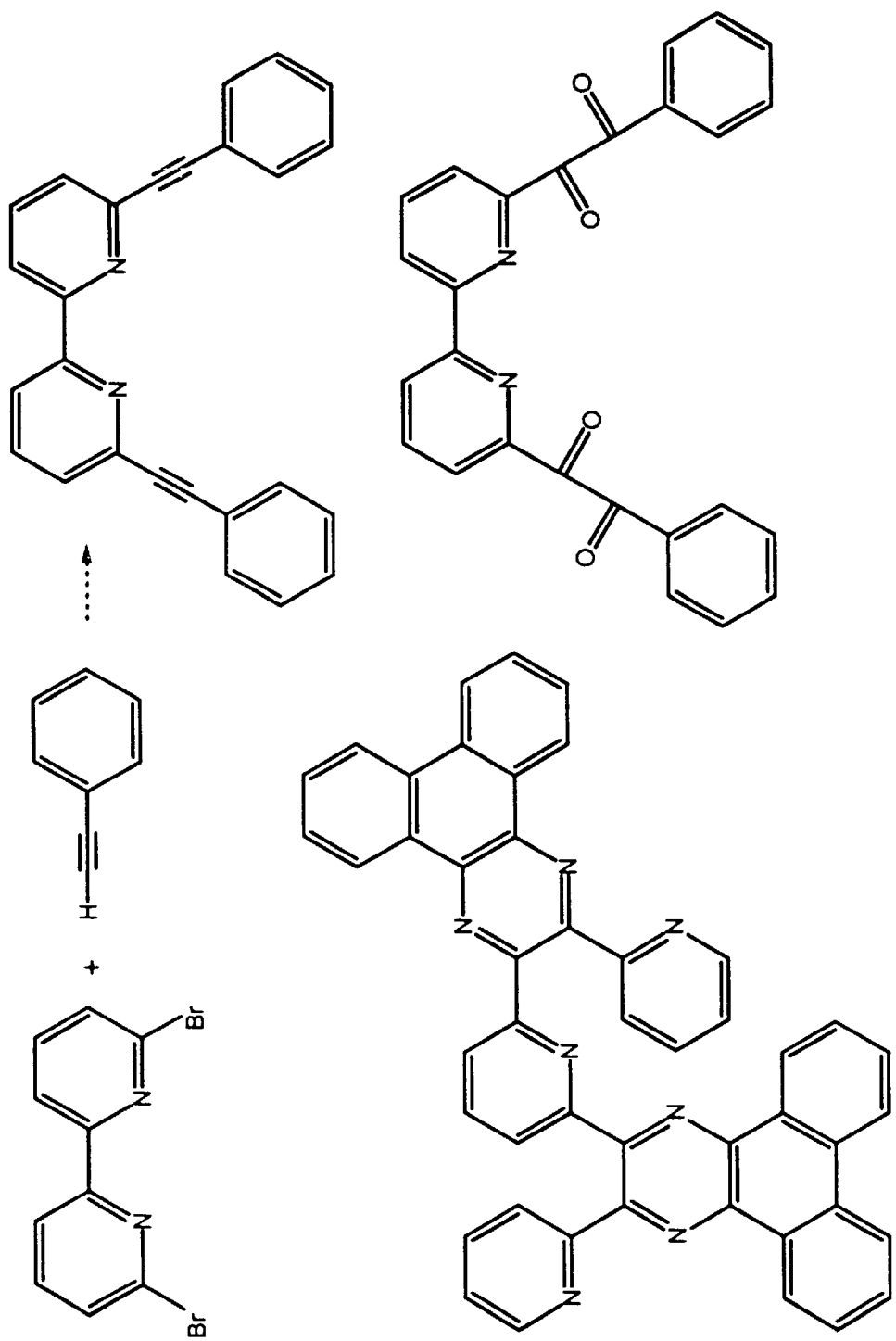
FIG. 24 illustrates a reaction scheme for the preparation of a dimer of pyridine-dibenzoquinoxaline.
Figure 25:
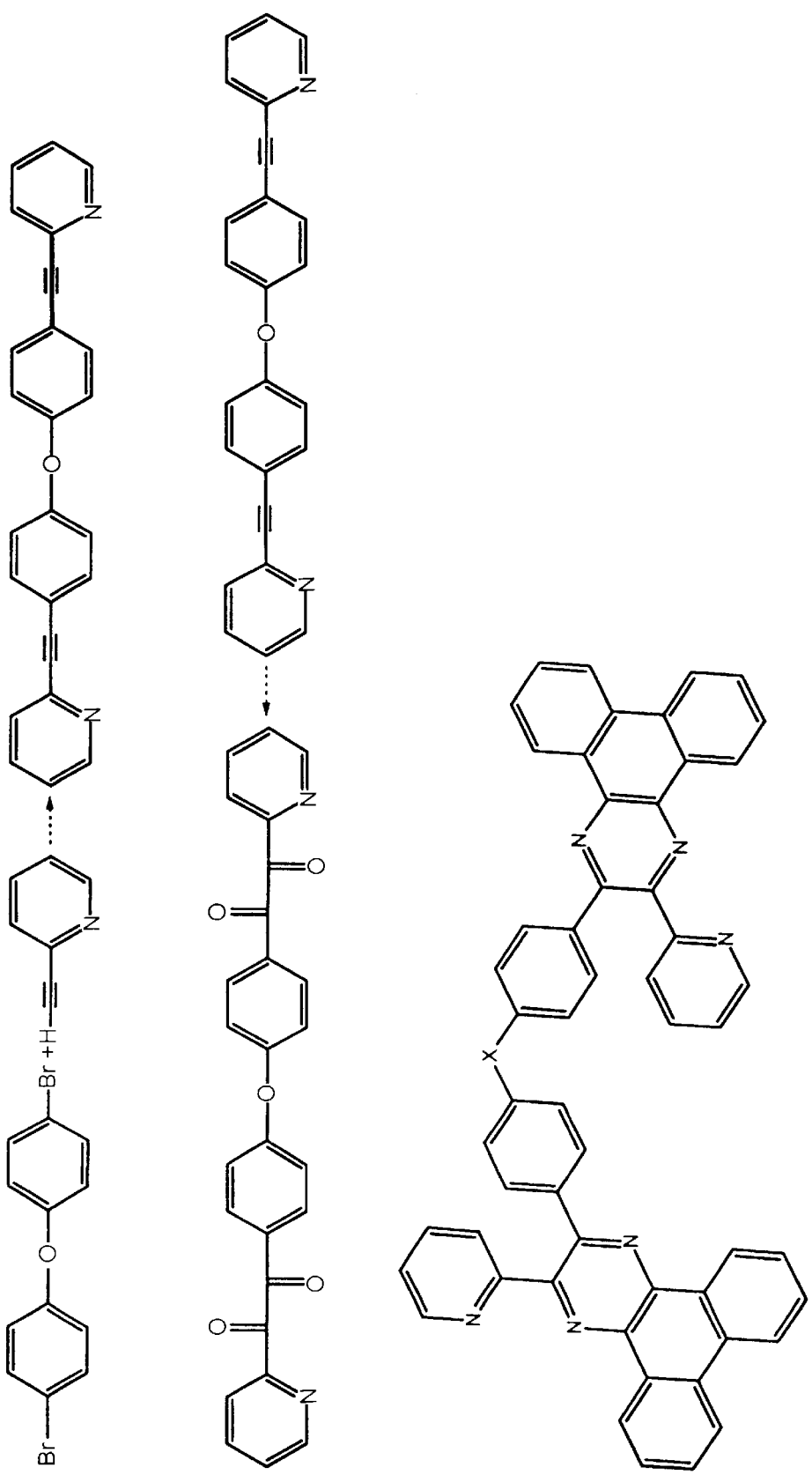
FIG. 25 illustrates a reaction scheme for the preparation of a dimer with various linkages.

Branched and non linear quinoxaline compounds are also useful in the invention. One approach to obtain morphologically stable materials is to build up chromophors with bulky steric geometry. The preparation of a dibenzoquinoxaline dimer is illustrated in FIG. 23. Dimers with more complicated structures involves the use of multi-step preparation methods as shown in FIGS. 24 and 25. The preparation of a pyridine-dibenzoquinoxaline dimer is illustrated in FIG. 24, and the preparation of a dimer with various linkages is illustrated in FIG. 25.

Useful branched and non-linear dibenzoquinoxaline compounds include compounds of formulas 1 to 11, shown below, where X is preferably pyridyl, phenyl, thiophene, or their alkyl and alkoxyl substituted derivatives, and, more preferably, pyridyl and phenyl. Preferably, R1 and R2 are alkyl with from 1 to about 4 carbons, and, more preferably, methyl.

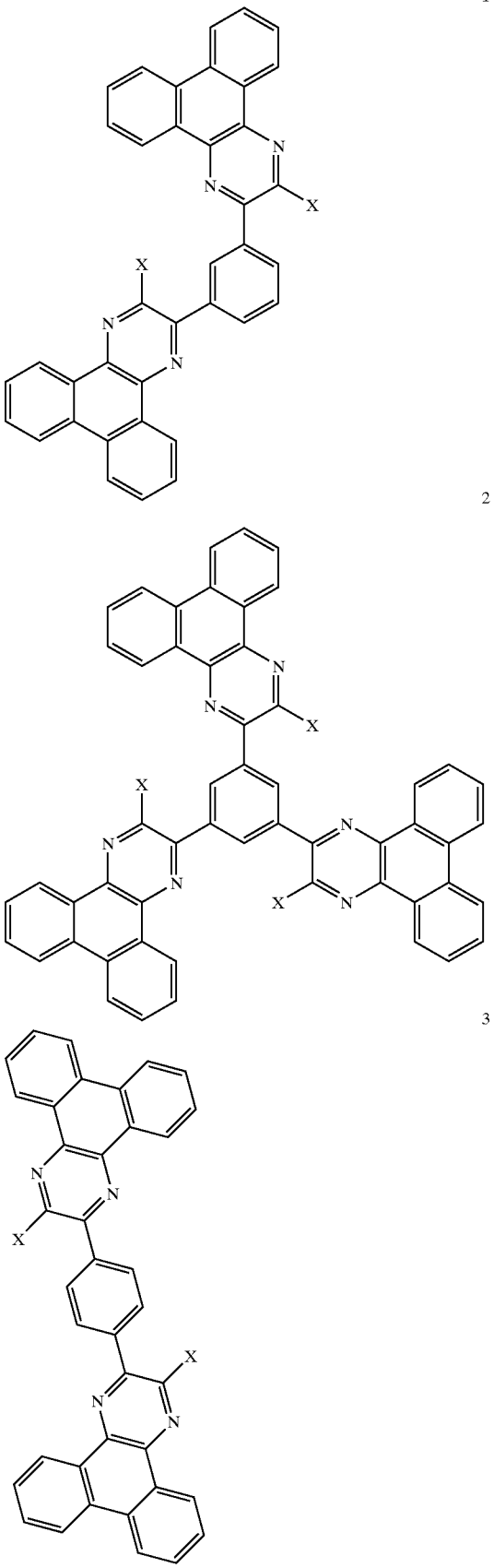

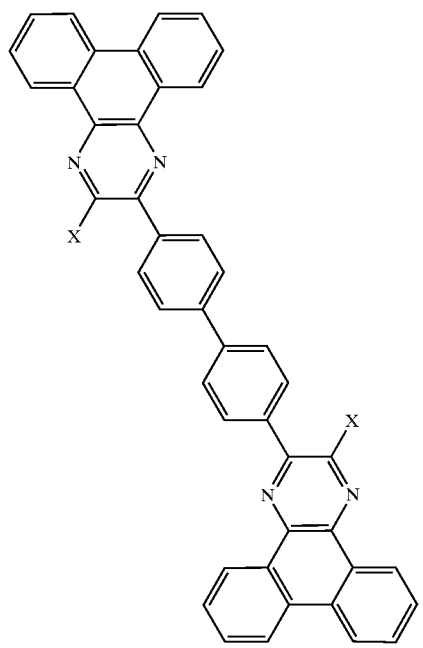
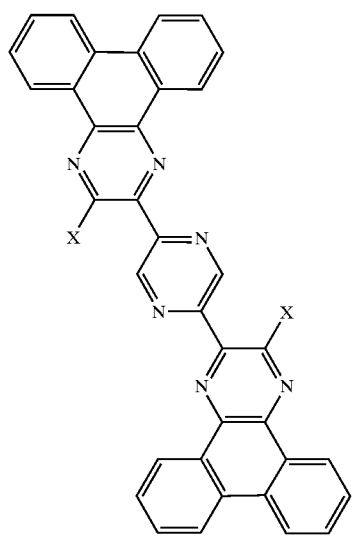
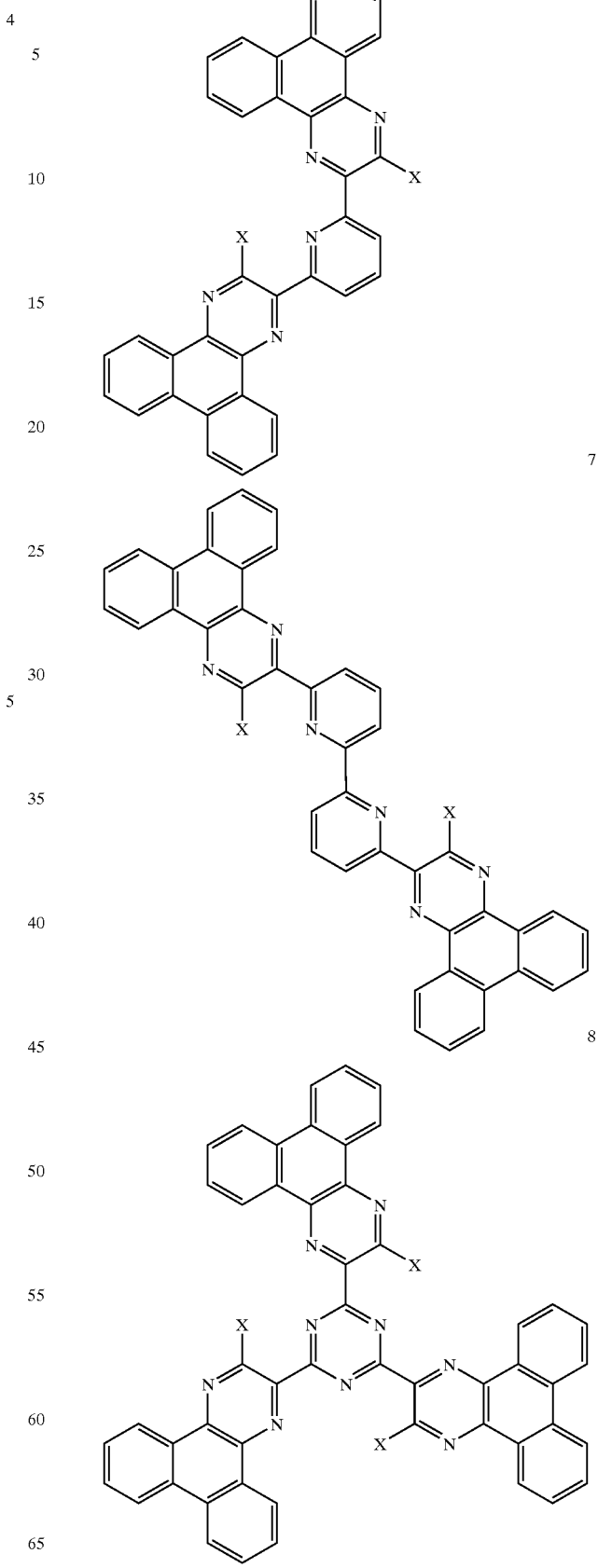

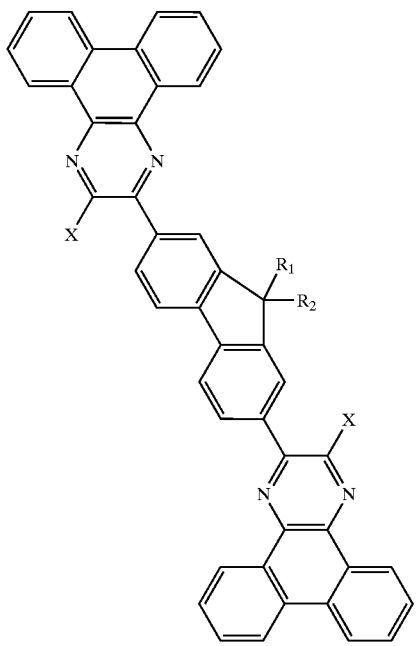

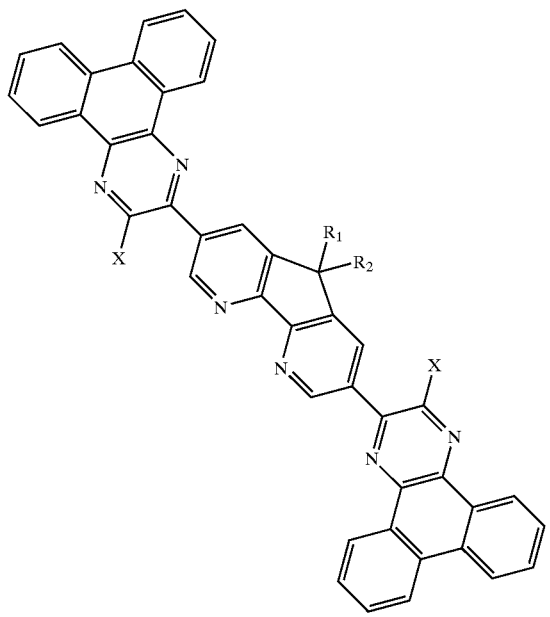

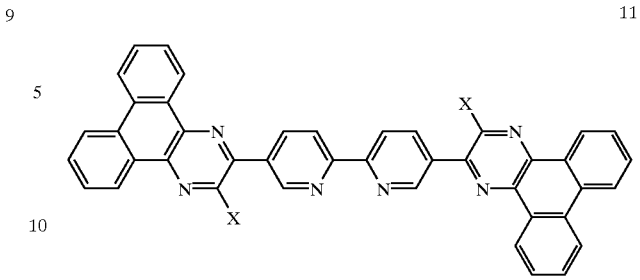

X: aryl, heteroaryl, alkyl with C=1–20
R1, R2=H, alkyl with C=1–20, aryl, heteroaryl While it is apparent that the invention disclosed herein is well calculated to fulfill the objects stated above, it will be appreciated that numerous modifications and embodiments may be devised by those skilled in the art. Therefore, it is intended that the appended claims cover all such modifications and embodiments that fall within the true spirit and scope of the present invention.

What is claimed:

1. An organic light emitting device, comprising an anode, a cathode, and at least one layer positioned between the anode and the cathode, wherein the at least one layer comprises 2,3-di-pyridin-2-yl-dibenzoquinoxaline.

2. The organic light emitting device of claim 1, wherein the device is a three layer ITO/α-NPD/AlQ$_3$/ETL/Li—Al OLED, where ITO is an indium tin oxide coated glass substrate anode, α-NPD is an N,N'-dinaphthlene-N,N'diphenyldiaminobiphenyl hole-transporting layer, AlQ$_3$ is an 8-hydroxyquinoline aluminum emissive layer, and ETL is an electron-transporting layer comprising 2,3-di-pyridin-2-yl-dibenzoquinoxaline.

3. The organic light emitting device of claim 1, wherein the device is a two layer ITO/AlQ$_3$/ETL/Li—Al OLED, wherein ITO is an indium tin oxide coated glass substrate anode, AlQ$_3$ is an 8-hydroxyquinoline aluminum emissive layer, and ETL is an electron-transporting layer comprising 2,3-di-pyridin-2-yl-dibenzoquinoxaline.

4. The organic light emitting device of claim 1, wherein the device is a four-layer device comprising an electron-transporting layer comprising 2,3-di-pyridin-2-yl-dibenzoquinoxaline, an exciton blocking layer comprising 2,9-dimethyl-4,7-diphenyl-1,10-phenynanthroline, an emissive layer comprising a 4,4'-N,N'dicarbazole-biphenyl host material doped with fac tris(2-phenylpyridine iridium, and an N,N'-dinaphthlene-N,N'diphenyldiaminobiphenyl hole-transporting layer.

5. The organic light emitting device of claim 1, wherein 2,3-di-pyridin-2-yl-dibenzoquinoxaline is present in the at least one layer in an amount of at least about 1 percent by weight.

* * * * *

UNITED STATES PATENT AND TRADEMARK OFFICE
CERTIFICATE OF CORRECTION

PATENT NO. : 6,723,445 B2
DATED : April 20, 2004
INVENTOR(S) : Li et al.

It is certified that error appears in the above-identified patent and that said Letters Patent is hereby corrected as shown below:

Drawings,
Sheet 3, Figure 3, "Absorbaaaance" should read -- Absorbance --.

Column 1,
Line 14, "improvements" should read -- on improvements --; and
Line 35, "layers" should read -- layer --.

Column 2,
Line 54, "florins," should read -- fluorenes --.

Column 4,
Line 42, "derivative" should read -- derivatives --.

Column 6,
Lines 17 and 62, "-dibenzoquinoxaline," should read -- -dibenzo[f,h]quinoxaline, --.

Column 8,
Line 45, "-dinaphthlene-" should read -- dinaphthalene --.

Column 9,
Line 13, "red a" should read -- a red --.
Line 13, "electroluminenscence" should read -- electroluminescence --;
Line 24, "anthrene-dibeanzoquinoxaline" should
read -- anthracene-dibenzoquinoxaline --; and
Line 64, "electroluminenscence" should read -- electroluminescence --.

UNITED STATES PATENT AND TRADEMARK OFFICE
CERTIFICATE OF CORRECTION

PATENT NO. : 6,723,445 B2
DATED : April 20, 2004
INVENTOR(S) : Li et al.

It is certified that error appears in the above-identified patent and that said Letters Patent is hereby corrected as shown below:

Column 11,
Line 14, "is in" should read -- in --.

Column 16,
Lines 26, 32 and 38, "-dibenzoquinoxaline." should read -- -dibenzo[f,h]quinoxaline. --;
Line 29, "-dinaphthlene-N," should read -- -dinaphthalene-N, --;
Line 42, "dibenzoquinoxaline," should read -- dibenzo[f,h]quinoxaline, --;
Line 44, "iridium," should read -- iridium [Ir(ppy)$_3$], --;
Line 45, "N-dinaphthlene-N," should read -- N-dinaphthalene-N, --; and
Line 48, "-dibenzoquinxaline" should read -- -dibenzo[f,h]quinoxaline --.

Signed and Sealed this

Twenty-eighth Day of September, 2004

JON W. DUDAS
*Director of the United States Patent and Trademark Office*